(12) United States Patent
Yilmaz-Elis et al.

(10) Patent No.: US 12,180,471 B2
(45) Date of Patent: Dec. 31, 2024

(54) ANTISENSE OLIGONUCLEOTIDES FOR THE TREATMENT OF STARGARDT DISEASE

(71) Applicant: ProQR Therapeutics II B.V., Leiden (NL)

(72) Inventors: Aliye Seda Yilmaz-Elis, Leiden (NL); Peter Adamson, Leiden (NL); Kalyana Chakravarthi Dulla, Leiden (NL); Iris Antoinette Ernestine Schulkens, Leiden (NL)

(73) Assignee: ProQR Therapeutics II B.V., Leiden (NL)

( * ) Notice: Subject to any disclaimer, the term of this patent is extended or adjusted under 35 U.S.C. 154(b) by 1239 days.

(21) Appl. No.: 16/604,618

(22) PCT Filed: Apr. 13, 2018

(86) PCT No.: PCT/EP2018/059542
§ 371 (c)(1),
(2) Date: Oct. 11, 2019

(87) PCT Pub. No.: WO2018/189376
PCT Pub. Date: Oct. 18, 2018

(65) Prior Publication Data
US 2021/0115439 A1    Apr. 22, 2021

(30) Foreign Application Priority Data
Apr. 13, 2017 (GB) .................................. 1706009

(51) Int. Cl.
*C12N 15/113* (2010.01)
(52) U.S. Cl.
CPC ........ *C12N 15/113* (2013.01); *C12N 2310/11* (2013.01); *C12N 2310/315* (2013.01); *C12N 2310/321* (2013.01); *C12N 2310/322* (2013.01); *C12N 2320/33* (2013.01)
(58) Field of Classification Search
CPC .............. C12N 15/113; C12N 2310/11; C12N 2320/33
See application file for complete search history.

(56) References Cited

U.S. PATENT DOCUMENTS
6,531,456 B1    3/2003  Kurtzman

FOREIGN PATENT DOCUMENTS

| EP | 1619249 | 1/2006 | |
|----|---------|--------|---|
| EP | 2425814 | 6/2013 | |
| JP | WO02052044 A2 * | 7/2002 | ............... C12Q 1/68 |
| WO | WO 1998037764 | 9/1998 | |
| WO | WO 2002052044 | 7/2002 | |
| WO | WO 2012168435 | 12/2012 | |
| WO | WO 2013036105 | 3/2013 | |
| WO | WO 2015004133 | 1/2015 | |
| WO | WO 2015190922 | 12/2015 | |
| WO | WO 2016005514 | 1/2016 | |
| WO | WO 2016034680 | 3/2016 | |
| WO | WO 2016135334 | 9/2016 | |
| WO | WO2017106370 A1 * | 6/2017 | ........... C12N 15/113 |
| WO | WO 2017186739 | 11/2017 | |
| WO | WO 2018109011 | 6/2018 | |

OTHER PUBLICATIONS

Dulla et al. (Apr. 2018) "Oligonucleotide-Based Splice Correction of the ABCA4 c.5461-10T>C Mutation in Stargardt Disease Type", In: Investigative Ophthalmology & Visual Science (vol. 59, No. 9), 12300 Twinbrook Parkway, Rockville, MD 20852-1606 USA: Assoc Research Vision Ophthalmology Inc. (Year: 2018).*
Dorn et al. (2008) "Clinical application of CpG-, non-CpG-, and antisense oligodeoxynucleotides as immunomodulators" Current opinion in molecular therapeutics, 10(1), 10-20. (Year: 2008).*
Hammond et al. (2011) "Genetic therapies for RNA mis-splicing diseases" Trends in genetics, 27(5), 196-205. (Year: 2011).*
Kher et al. (2011) "Antisense oligonucleotides and RNA interference" Challenges in Delivery of Therapeutic Genomics and Proteomics, 325-386. (Year: 2011).*
Maugeri et al., "The 2588GrC Mutation in the ABCR Gene Is a Mild Frequent Founder Mutation in the Western European Population and Allows the Classification of ABCR Mutations in Patients with Stargardt Disease, " Am J Hum Genet., 1999, 64:1024-1035.
International Preliminary Report on Patentability in PCT Appln. No. PCT/EP2018/059542, dated Oct. 15, 2019, 8 pages.
Aukrust et al., "The intronic ABCA4 c.5461-10T>C variant, frequently seen in patients with Stargardt disease, causes splice defects and reduced ABCA4 protein level," Acta Ophthalmol., 2017, 95(3):240-246.
Albert, et al., "Abstract P243: ABCA4 mRNA analysis of iPSC-derived photoreceptor cells of Stargardt patients reveals protein-truncating non-canonical and deep-intronic splice site variants," Human Gene Therapy, 2016, 27(11):A119.
Dalkara, et al., "Let there be light: gene and cell therapy for blindness," Human Gene Therapy, 2016, 27(2):134-147.
Schulz, et al., "Mutation spectrum of the ABCA4 gene in 335 Stargardt disease patients from a multicenter German cohort—impact of selected deep intronic variants and common SNPs," Invest. Ophthalmol. Vis. Sci., 2017, 58(1):394-403.
Tanna, et al., "Stargardt disease: clinical features, molecular genetics, animal models and therapeutic options," Br. J. Ophthalmol., 2017, 101:25-30.
Aukrust, et al., "The intronic ABCA4 c.5461-10T>C variant, frequently seen in patients with Stargardt disease, causes splice defects and reduced ABCA4 protein level," Acta Ophthalmol., 2016, 24:1-7.

(Continued)

Primary Examiner — Teresa E Knight
Assistant Examiner — James Joseph Graber
(74) Attorney, Agent, or Firm — Fish & Richardson P.C.

(57) ABSTRACT

The invention relates to the fields of medicine and biotechnology. In particular, it relates to novel antisense oligonucleotides (AONs) that may be used in the treatment, prevention and/or delay of Stargardt disease and/or ABCA4-associated eye disease. More in particular, the invention relates to AONs that are used in inhibiting or blocking exon 39 skipping in the human ABCA4 pre-mRNA.

5 Claims, 14 Drawing Sheets

Specification includes a Sequence Listing.

(56) References Cited

OTHER PUBLICATIONS

Cirak, et al., "Exon skipping and dystrophin restoration in patients with Duchenne muscular dystrophy after systemic phosphorodiamidate morpholino oligomer treatment: an open-label, phase 2, dose-escalation study," Lancet, 2011, 378(9791):595-605.

Cirak, et al., "Restoration of the Dystrophin-associated glycoprotein complex after exon skipping therapy in Duchenne muscular dystrophy," Mol. Ther., 2011, 20:462-467.

Dorn and Kippenberger, "Clinical application of CpG-, non-CpG-, and antisense oligodeoxynucleotides as immunomodulators," Curr. Opin. Mol. Ther., 2008, 10(1):10-20.

Dotsenko, et al., "Hageman factor and kallikrein in pathogenesis of senile cataracts and the pseudoexfoliation syndrome," Immunopharmacology, 1996, 32:141-145.

Egholm, et al., "PNA hybridizes to complementary oligonucleotides obeying the Watson-Crick hydrogen-bonding rules," Nature, 1993, 365:566-568.

Goemans, et al., Systemic administration of PRO051 in Duchenne's muscular dystrophy, N. Engl. J. Med., 2011, 364(16):1513-1522.

Gorman, et al., "Stable alteration of pre-mRNA splicing patterns by modified U7 small nuclear RNAs," Proc. Natl. Acad. Sci. USA, 1998, 95(9):4929-34.

Govindaraju and Kumar, "Backbone-extended pyrrolidine peptide nucleic acids (bepPNA): design, synthesis and DNA/RNA binding studies," Chem. Commun., 2005, 495-497.

International Search Report and Written Opinion in PCT Appln. No. PCT/EP2018/059542, dated Sep. 24, 2018, 15 pages.

Morita, et al., "2'-O, 4'C-Ethylene-bridged nucleic acids (ENA) with nuclease-resistance and high affinity for RNA," Nucleic Acid Res., 2001, Suppl. 1: 241-242.

Nielsen, et al., "Sequence-selective recognition of DNA by strand displacement with a thymine-substituted polyamide," Science, 1991, 254:1497-1500.

Sangermano, et al., "Photoreceptor progenitor mRNA analysis reveals exon skipping resulting from the ABCA4 c.5461-10T>C mutation in Stargardt disease," Ophthalmology, 2016, 123(6):1375-1385.

Scaffidi and Misteli, "Reversal of the cellular phenotype in the premature aging disease Hutchinson-Gilford progeria syndrome," Nat. Med., 2005, 11(4):440-445.

Suter, et al., "Double-target antisense U7 snRNAs promote efficient skipping of an aberrant exon in three human beta-thalassemic mutations," Hum. Mol. Genet. 1999, 8(13):2415-23.

* cited by examiner

Fig.2A

<-- Intron 38 -->                                                                  >  Exon 39 -->
GCCUUGCCCUGUGCUGUGUCCUGUGAGAGCAUCUGGGCCCCACCUGCUGAAGAGAGGGGGUGGGGGGUUUGCCCCGUUUCCAACAGUCCUACUUCCCUGUUUCAGACGCUGCUC...
3'-AACGGGACACGACAGGACACUC-5' (1)
            3'-UCGUAGACCCGGGGUGGACGAC-5' (2)
                      3'-UUCUCUCCCCCACCCCAAAC-5' (3)
                                        3'-GGGGCAAAGGUUGUCAGGAUG-5' (4)
                                                      3'-AAGGGACAAAGUCUGCGA-3' (5)
                                                                   (6) 3'-AAAGUCUGCGACGAG...

3'-ACGACAGGACACUCUCGUAGACC-5' (17)
                                      3'-ACACUCUCGUAGACCCGGGGUGG-5' (18)
                                              3'-GUAGACCCGGGGUGGACGACUUCU-5' (19)
                                                     3'-GGGGUGGACGACUUCUCUCCCC-5' (20)
                                                             3'-ACGACUUCUCUCUCCCCCACCC-5' (21)
                                                                    3'-CCAAACGGGCAAAGGUUGUCAG-5' (22)
                                                                           3'-CAAAGGUUGUCAGGAUGAAGGGAC-5' (23)
                                                                                  3'-GGAUGAAGGACAAAGUCUGCGA-5' (24)
                                                                                               (25) 3'-AAGUCUGCGACGAG...

AGGUUCAACGCCGUGAGGAAGCUGCUCAUUGUCUUCCCCACUUCUGCCGGGCCCUGGGCCCUGCACUGAGCCAGGCUGUGACAGAUGUCUAUG...
...UCCAAG-5' (6)
    3'-GGCACGACUCCCUUCGACGAGU-5' (7)
             3'-GAAGGGGUGAAGACGGACCC-5' (8)
                       3'-CCCCGGAGUAACUGGAACGUUG-5' (9)
                                          (10) 3'-UCUACAGAUAC...

...UCCAAGUUG-5' (25)
       3'-UCCUUGACGAGUAACAGAAGGG-5' (26)
              3'-GUGAAGACGGACCCGCCCCGGA-5' (27)
                      3'-UAACUGGAACGUGACUCGGUCCG-5' (28)
                                          (29) 3'-AGAUAC...

Fig.2B

Intron 39 -->
...CCCGGUUUGGUGGGGUGGGUAGCCGAGGCAUGGGCCCCAUGGAGCCCCUGGGUCCAAAGCUGGAGGGUACCGGGGGGCUCCCUGCAUCAGACUGUGGCAGGGCUGGUGCU...

...GGGCCAAAC-5' (10)
3'-CCAAACCACCCACCAUCGGCUC-5' (11)
3'-CGGGUACCUCUGUACCCGGGACCC-5' (12)
3'-AGGUUCGACCCUCCCAAUG-5' (13)
3'-ACCUCCCAAUGGCCCCCCGAG-5' (14)
(15) 3'-CUGACACCGUCCCCGACCACGA-5'
3'-CCGAGGACGUAGUCUGACACCGU-5' (16)

...GGGCCAAACCACCCCCACCA-5' (29)
3'-AACCACCCACCAUCGGCUCCGGG-5' (30)
3'-ACCAUCGGCUCCGGGUACCCGGG-5' (31)
3'-GGCUCCGGGUACCUCGUACCCGGGU-5' (32)
3'-ACCUCGUACCCGGGCCCAGGUUUC-5' (33)
3'-CGGGCCCAGGUUUCGACCCUCCC-5' (34)
3'-UCCCAAUGGCCCCCCGAGGACG-5' (35)
3'-CCCCGAGGACGUAGUCUGAGACAC-5' (36)
3'-CGUAGUCUGACACCGUCCCCGAC-5' (37)

...AGGAGGGGACCUGUGGGCUGGAGGUGCCCUCUGUUCCAUGGCUGGCCACAGGAGGAUGGAGGGAGCCACAGGAGGAUGGAGGGAGCAGCCCUUAUG...

...AGGCGGGUGUUGGCUCUUGCUCUCAGUUCCCACAUAAGGCCUGGUGGGCCCAGGUCUGUGGGCUGGAAGUGGACUCAAU...

Exon 40 -->
...UCCUGUGAUGCCCAGGUGAGCACUCUGCAAAUCCGUUCCACGUUCCACGGGACCUGAUGGGAAGAAACCUGUGUUGCCAUGGUGGAAGGGUGGUGUACUUCCUCUG...

...ACCCUGCUGGUCCAGCGCCACUCUCCUCUUCCCAAUGGGCCAGUGCCAUGCCUCCAGCCAUCCAGUGGGCCAGCUCCAGAACUGGACCCUUAUACCCACAUG...

Intron 40 -->

...GUCAUUUCUUUCCUCAGGAGCCCCA-3'

Fig.3A gugagcauaacuuucuuggcuuuuuuguuugauuaguaggauaguagaguaugug uuggucgagcagagccagg
ggcaagcaucguacauguagcagcuguaugcggaugagugccacuuucuuccucccuaccccgacccugccuccu
uuccuuccuuccuuccucccauccuuccuuccucuuuccuucuucuccucccuccucccuccuuccccgucccuccu
uccuuccuuuucauugcuuccuuccuuccuucgucccuccuucccuuccucuuuccuucugcccucucucccuuuu
uccuuucauccucccuccauccucccuccauccuuccuucuuucuuccuucuuuccuuccauaagcaccuuuuuc
auuucgugcucugaaugaaaugguuucguguuuauucugcaagcaaaacuugauucuugcaauaaacuuua
agcuuugcuuacucuuucagaaagguuuucucagggacuuggguguugggu uuuacacacacacaucaauac
auuuggguaauuucaaaaucuaaaaggaacaaaaggcauacaaugaaaaaaucuccuuccuaccccuguuuccc
acucaugcaguucucuuccagaggcaaacucuuacuugaguuuccugugugcucuggagacacaucagcagau
cccuauacggucuuucucccgcuuucuuauggaaauuguaacacucugacauauacuauuccuugggcaaguuaa
ucuugaugaagagacuggguguuccaugcugaaugccucacuuuaugagcugccaagcccaguugucccuuc
caccugaccuccccuguccagagacagauggccaaacugaaucauaaaaagaggggaaaaaagaaggcaguc
gcugcagggcugucuuuacuccacacuccacacucccaguccccaccgcugugucugaguccuggcuguggcuguc
cuuggaacauugccucaccacgugccugucccaggcgccucaaccuuccucuccauuagcucuucccag
uucagaggugggaccggccagcacaucugcacugcugcccugccacacccaccuccaccugccucugggccccacu
ggggaacacaggacaaaucgugcggaggccccaccaugaaccgcccagacccguggaccccugagacugacucuu
uccagaucuuguuaggguuucguggcugcuaggcaaguaacgaagccucaucuguccaugaaugauaagaaauu
cagcaugucagagucagacucuggaaaggcgggggga uaagaacacagcccagcagauggccagagcacccagg
ugacugaaagugcugcuuugcagagcuguguuugccacaggcucacagcccacuaagucuuaagacaguuuuccu
ucagaauaauuaaauagccagcuuaaagcaacucagaacauuuccccucugaggcugcacccauuuagccaaca
uuugcuaagcacccgccuucaaaaaccugguauuuucaugaaauuauccgauacacagcugcuauggaaacccc
caguaucccacaggaagcuccccagcucccagcagcugccggcccgugugagaucaggaggucuuuaccagcugaa
caccacgugccgggugugugcugauauaaacaagcguggcccacucguccugccuccagaggcucccguuccagu
cggaaaaggaccugcccacgaaguuugcaacgauauaagccacaguguaugauccuccauaauacagcgugugac
agagcagcagaggagcgaggcagauaacaugcugcaggccagaggcagcgggaagagccaggcugcaggggcugg
gggagccgguggaggaaguucaauuucagccuguagauuucuauuagcccauuuaauaaauaaugaagugcc
uacucgagcuaaucaugugcagguauuuaggaaggacaaaaaaauaauuaggacucagugcccacccuccagg
ggcccacugacuaguagagaaaguaggcagauuuuaaaaaauuaaucaugggaaugugauaagugcugggaga
gaggaauggauacuuucucaugggaaucuuggaaggcuuguaagggaaggcacucucugagccagcugucuaaag
aagaacaggaaucuuuaagaaagcagaagggaaaagagcauucuuccugcuuggagcaauagguaacagccugc
acaugcccaggccuagaggccaaagagcacagugauuccagaaagaguggggagaaagg guaggcagggaaggau
gagguaaugugggcgcaggguguggaggcuggagaggaggagguuguggga cugggaggagccagauggaaugg
acagcagugcccagccaggagcuaugcuggccucguacgccucgaugucccuucuauuucucaggggaggcucu
gcccaacaugccaagucc gaccacuugaaaacaaguccc uggcuuaacacagaccccagagagagucuccaacccu
ccucucccuagacaaugguaguugcccugugaggggcugaaaagcagagcuggagaug gcucagggccuggugu

Fig.3B aacaaaugccuugagggcuccuguuguuucaaagugagucugcagggagagcucccuaaguggacagcaggaggg
cugcagcuucucugcacauuccugcugucaccccagagucaccaggggaggguaaggacaguaaugcagguu
ccucacaguuagccucggugcccacaugguacugagcauaguaaauguuuagaagaugcugccuggcuagacaaa
ggggaagcucccgcccacuagaaacuugcagggagccccaguccuugauggucauuuaauugauuagcuccuug
gccuggccuugaggcacugcuuguaaguacuugaccuccauugcaaacccaugaugcucugcuggacaaaucc
cuccaguggccagucuggcugcaaggacucucugucugcaggccuugcccugugcuguccugugagagcaucggg
ccccaccugcugaagagagggggggugggguuugccccguuccaacaguccuacuucccuguuucagACGCU
GCUCAGGUUCAACGCCGUGCUGAGGAAGCUGCUCAUUGUCUUCCCCACUUCUGC
CUGGGCCGGGGCCUCAUUGACCUUGCACGAGCCAGGCUGUGACAGAUGCUAUG
CCCGGUUUGgugggugguagccgaggcccauggagcaugggcccuggguccaaagcugggagguuaccggg
ggggcuccugcaucagacuguggcaggggcuggugcuaggaggggaccuuguugggcuggaggguguccugccagc
uggagaggauuagggugccucuguuccauggcuggggagccacaggagggauggagggcagcccuuaugaggcg
gguguuggcucuugcucaguucccacauaaggccuggucuaguggggcccugugcuguggccaggucuguggggu
gagcuggggcggcugaaguggacucaauuccuguugaugcccag*GUGAGGAGCACUCUGCAAAUCCG*
*UUCCACUGGGACCUGAUUGGGAAGAACCUGUUUGCCAUGGUGGUGGAAGGGGUGG*
*UGUACUUCCUCCUGACCCUGCUGGUCCAGCGCCACUUCUUCCUCCCAAUG*guacg
uccaugccacacccugggccaguggggcagcucagggcauccagaacuggaccuuauacccacauggucauucuuu
ccucaggagccccacuccacaauguuuuucuacauucuaaagccuggcuuuucuccaauaauacaaguagagg
aucgggguuaaaauaggcacauucaaauaugugaagagcauccacuuuaaauauuuaaaaaugcagugcauuaa
uuucaauugcugauauuuaauccuucuuauuuaauuaccaaauguguauuugauuagaugauaguauugcaaa
uaacaaugguuacaggguauccaaaguacuaggaaauagacaauguauuugagagaaaggacacagcaggc
cccuuugcuaauuagagauuugggagcaugggaguaauagggagccaugugaggggugcgggcagugaucac
gaccccccacuccuggaggaaggugggguagcugccaacccugacuuugaccagggcuucucaaaugccagguuag
cuggcaauugccauucuuccgcaggcucuuccugaagcuggguggggccccugccucacucccucugcaauccagu
ccuaccuuuauugccucacccaggggccugaauugccaagcagcagcccuuccuagcaagcuuuccccaauagug
uuuuguuucuuaacuuuuccuccucucaggcugagugugguucaccuguaaauagauuccaaggacuugguuuuau
guuuugauccacagggaauugauuuauggaaaugaaucugccuuucuacucacaggacugugagaggugaaug
agaucacaggugucaacacacgccugaugaaacaggauacacaagcaguucuaguuaugggagacagugucagga
auuguguccuuggcacccucagccccugcagacccuuucugcagccuggccauaccuuuuagaggcuuuugugu
gggagagagcaggucaggagguugacuacccaaauugacucauuagcuucaaacucugaugucaacacauuugaa
ugaguccugccugcuuuagggccuaaagaggaccagagaaguacaccauaguccuggcuuccagaaggucaggg
aggguuucaaagaagaggcugugucuuuaagaaugggggaagauuccauuggugggcaggaggaggagaacau
ugagggacuggaaacacaugcggaggcugggagacgggaaugaccauaggacugggaaccaggggagaugcca
auugcugacagaggaguuagugcaagagguaagugagaagggguaggugggcuggauugcagggcuguaacuac
agcugcagagggagggcuucaaccuacagcugaugggggaacaacagaagguuuugaggcaugagguggccugaug

Fig.3C acaacucuguuuuggaaagguggaguuggcagggcagacuggaggaaguggaggcucggagguuaguaacuac
cccuuacugagugcuugcuguagaggaagcauuuuaguccugacggugaucccaggcccugagucuuuacucugu
gccaggcacugugcugaguucaucuucagcacaauccaugagacagguauuguuacccuccuccucaucacaugg
uugaaguaggcaagguucagagagguccaaugcccaagaucacaugaggaggccaggacuggaacccaaggcu
gacucuggacaugagcaccugaccucucuaccuaaugccuaaugccucuccugcugggagcccuuuuuagaauuua
agucuuaaaggauggaagcccagaaggaagcagaagcaaggaaguggaagagaggucccauggaaaggacagug
ccaaggacacuguacagccagcccaauccugaccccuuuucuucaucuag

Fig.8 gaattc**cggaggtcaacaacgagtcttttgtcatctacatgttcgtggtccacttcaccatc
cccatgattatcatcttttctgctatgggcagctcgtcttcaccgtcaaggag**gtacgggc
cggggggtgggcggcctcacggctctgaggtccagcccccagcatgcatctgcggctcctg
ctccctggaggagccatatcacaagtttgtacaaaaagcaggcttc<u>gtgttaacaaatgcc
ttgagggctcctgttgtttcaaagtgagtctgcagggagagctccctaagtggacagcagga
gggctgcagcttctctgcacattcctgctgtcaccccagagtcacctaggggaggggtaag
gacagtaatgcaggttcctcacagttagcctcggtgcccacatggtactgagcatagtaaat
gtttagaagatgctgcctggctagacaaaggggaagctcccgcccactagaaacttgcaggg
agccccagtccttgattggtcatttaattgattagctccttggcctggccttgaggcactgc
ttgtaagtacttcatgacctccattgcaacccatgatgctctgctggacaaatccctccag
tggccagtctggctgcaaggactctctgtctgcaggccttgccctgtgctgtcctgtgagag
catctgggccccacctgctgaagagagggggggtggggtttgcccgtttccaacagtccta
cttccctgtttcag</u>ACGCTGCTCAGGTTCAACGCCGTGCTGAGGAAGCTGCTCATTGTCTTC
CCCCACTTCTGCCTGGGCCGGGGCCTCATTGACCTTGCACTGAGCCAGGCTGTGACAGATGT
CTATGCCCGGTTTG<u>gtgggtggtagccgaggcccatggagcatgggccctgggtccaaagct
gggagggttaccggggggctcctgcatcagactgtggcaggggctggtgctaggaggggac
cttgttggctggaggtgtcctgccagctggagaggattagggtgcctctgtttccatggct
ggggagccacaggagggatggagggcagcccttatgaggcgggtgtttggctcttgctcagt
tcccacataaggcctggtctagtgggccctgtgctgtggccaggtctgtggggtgagctgac
ccagctttcttgtacaaagtggtgatgagaggtacctccgaggggtaaacagttgggtaaac
agtctctgaagtcagctctgccattttctagctgtatggccctgggcaagtcaatttccttc
tctgtgctttggtttcctcatccatagaaaggtagaaagggcaaaacaccaaactcttggat
tacaagagataatttacagaacacccttggcacacagagggcaccatgaaatgtcacgggtg
acacagccccttgtgctcagtccctggcatctctaggggtgaggagcgtctgcctagcagg
ttcccaccaggaagctggatttgagtggatggggcgctggaatcgtgagggcagaagcagg
caaagggtcggggcgaacctcactaacgtgccagttccaagcacactgtgggcagccctggc
cctgactcaagcctcttgccttccag</u>**ttccggaactgcatgctcaccaccatctgctgcggc
aagaacccactgggtgacgatgaggcctctgctaccgtgtccaagacggagacgagccaggt
ggccccggcctaa**gacctgcctaggactctgtggccgactataggcgtctcccatcccctac
acctgtcgac

ANTISENSE OLIGONUCLEOTIDES FOR THE TREATMENT OF STARGARDT DISEASE

CROSS-REFERENCE TO RELATED APPLICATIONS

This application is a U.S. National Stage Application under 35 U.S.C. § 371 and claims the benefit of International Patent Application No. PCT/EP2018/059542, filed on Apr. 13, 2018, which claims the benefit of priority to GB Patent Application No. 1706009.6, filed on September Apr. 13, 2017; the disclosures of the foregoing are incorporated herein by reference in their entirety.

SEQUENCE LISTING

This application contains a Sequence Listing that has been submitted electronically as an. txt file named "SequenceListing.txt". The.txt file, created on Oct. 8, 2019, is 31,543 bytes in size. The material in the.txt file is hereby incorporated by reference in its entirety.

FIELD OF THE INVENTION

The invention relates to the field of medicine and biotechnology. In particular, it relates to antisense oligonucleotides (AONs) that are applicable in the treatment, prevention and/or delay of eye diseases, preferably macular dystrophy, more preferably Stargardt disease.

BACKGROUND OF THE INVENTION

Stargardt disease (STGD or STGD1) is the most common inherited macular dystrophy causing progressive impairment of central vision, with onset typically in childhood or young adulthood, and least frequently in later adulthood, with a better prognosis generally associated with a later onset. The disease has a prevalence of 1 in 8,000-10,000 and has an autosomal recessive mode of inheritance associated with disease-causing mutations in the gene coding for the photoreceptor cell-specific ATP-binding cassette transporter ABCA4. The protein contains 2273 amino acids, is predominantly expressed in the retina and localizes to the rims and cone outer segments disks. It is thought to flip N-retinylidene-phosphatidylethanolamine from the luminal to the cytosolic face of the photoreceptor disks. Stargardt disease links tightly with a massive deposition of lipofuscin content in the retinal pigment epithelium, failure in toxic substance removal and significant loss in photoreceptor cells. A major component of lipofuscin, di-retinoid-pyridinium-ethanolamine is formed when ABCA4 is missing or dysfunctional. Indeed, multiple reports have been published that confirmed that ABCA4 is the gene underlying Stargardt disease, showing a large number (1000) of disease-causing variants, of which more than half have been described only once. Biallelic variants in ABCA4 have been identified in approximately 75% of cases with Stargardt disease and in approximately 30% of patients with autosomal recessive come-rod dystrophy (CRD). The majority of mutations are missense, followed by nonsense mutations, small insertions/deletions, and mutations affecting RNA splicing. An unusually high proportion of Stargardt disease cases from northern Europe and the United States (~30%) is the result of only one ABCA4 variant. It was recently shown that the third most frequent ABCA4 variant, c.5461-10T>C present in intron 38, causes a severe form of Stargardt disease due to skipping of exon 39, or skipping of exon 39+exon 40 in the mRNA of ABCA4 (Aukrust et al. The intronic ABCA4 c.5461-10T>C variant, frequently seen in patients with Stargardt disease, causes splice defects and reduced ABCA4 protein level. *Acta Ophthalmol* 2016 Oct. 24:1-7; Sangermano et al. 2016. Photoreceptor progenitor mRNA analysis reveals exon skipping resulting from the ABCA4 c.5461-10T>C mutation in Stargardt disease. *Ophthtalmology* 123 (6):1375-1385). The skipping of exon 39 results in a frameshift deletion of 124 nucleotides, whereas the double skip of exon 39 and 40 results in a frameshift deletion of 254 nucleotides. Notably, such shorter versions of the protein were not detected, likely because they are unstable (Aukrust et al. 2016). It is estimated that approximately 7000 Stargardt disease patients in the Western world suffer from this particular mutation.

The three main routes of intervention to treat Stargardt disease are currently stem cell therapy, gene replacement therapy and different pharmaceutical approaches. A relatively new therapeutic development for treating inherited eye diseases is the use of antisense oligonucleotides (AONs), which target the pre-mRNA transcribed from the mutant gene. AONs are generally small polynucleotide molecules (16- to 25-mers) that are able to interfere with splicing as their sequence is complementary to that of the target pre-mRNA molecule. The envisioned mechanism is such that upon binding of the AON to a target sequence, with which it is complementary, the targeted region within the pre-mRNA interferes with splicing factors which in turn results in altered splicing. Therapeutically, this methodology can be used in two ways: a) to redirect normal splicing of genes in which mutations activate cryptic splice sites and b) to skip exons that carry (protein-truncating) mutations in such a way, that the reading frame of the mRNA remains intact and a (partially) functional protein is made. Both methods have already been successfully applied in patients with severe genetic disorders (Scaffidi and Misteli. 2005. Reversal of the cellular phenotype in the premature aging disease Hutchinson-Gilford progeria syndrome. *Nat. Med* 11(4):440-445; Cirak et al. 2011. Restoration of the Dystrophin-associated Glycoprotein Complex after Exon Skipping Therapy in Duchenne Muscular Dystrophy. *Mol Ther* 20:462-467; Cirak et al. 2011. Exon skipping and dystrophin restoration in patients with Duchenne muscular dystrophy after systemic phosphorodiamidate morpholino oligomer treatment: an open-label, phase 2, dose-escalation study. *Lancet* 378(9791):595-605; Goemans et al. 2011. Systemic administration of PRO051 in Duchenne's muscular dystrophy. *N Engl J Med* 364(16):1513-1522). With respect to eye diseases, AONs have been shown to be promising for the treatment of Leber's congenital amaurosis, or LCA (WO 2012/168435; WO 2013/036105; WO 2016/034680; WO 2016/135334). Further, WO 2016/005514 discloses exon skipping AONs for targeting the USH2A pre-mRNA, directed at skipping of exon 13, exon 50 and PE40, and/or retaining exon 12, for the treatment, prevention or delay of Usher syndrome type II. WO 2015/004133 discloses the use of an AON in the skipping of exon 10 from the ABCA4 pre-mRNA, for the treatment of Stargardt disease. Hence, although AONs have been described for exon skipping in the treatment of several inherited eye diseases including Stargardt disease, there appears to be a strong need for AON-based strategies in the treatment of Stargardt disease, especially when it relates to exon retention, more in particular for the treatment of Stargardt disease caused by the c.5461-10T>C mutation that induces exon 39 skipping.

SUMMARY OF THE INVENTION

The present invention relates to antisense oligonucleotides (AON) for use in the treatment, delay or prevention of Stargardt disease. More in particular it relates to an AON that is able to inhibit skipping of at least one exon, preferably exon 39, in human ABCA4 pre-mRNA, wherein the exon skipping is due to an (intronic) mutation in the ABCA4 gene, such as the c.5461-10T>C mutation in intron 38. Preferably, the AON is able to inhibit, prevent or block exon 39 skipping and/or exon 39/exon 40 double skipping. In a preferred embodiment, the AON of the invention comprises or consists of a sequence of any one of SEQ ID NO:1 to 37. The invention also relates to a pharmaceutical composition comprising an AON according to the invention, and a pharmaceutically acceptable carrier, wherein the pharmaceutical composition is for intravitreal administration. In yet another aspect, the invention relates to a viral vector expressing an AON according to the invention. In yet another aspect the invention relates to a nanoparticle or any type of slow-release composition comprising the AON of the present invention for efficient (and preferably long-lasting) release of the AON to the target tissue within the human eye. In another aspect, the invention relates to an AON according to the invention, a pharmaceutical composition according to the invention, or a viral vector according to the invention, for use in the treatment, prevention or delay of Stargardt disease. In yet another aspect, the invention relates to a method for the treatment of Stargardt disease or condition requiring modulating splicing of ABCA4 pre-mRNA (such as preventing the skip of exon 39 from ABCA4 pre-mRNA) of a human individual in need thereof, said method comprising contacting a cell of the human individual with an AON, a pharmaceutical composition or viral vector according to the invention and subsequently allowing the entry of said AON in said cell to then allow the inhibition of exon 39 skipping from the mutated human ABCA4 pre-mRNA present in said cell.

BRIEF DESCRIPTION OF THE DRAWINGS

FIGS. 2A-2B show the RNA sequence (from 5' to 3'; SEQ ID NO:50) of exon 39 and exon 40 (bold, both exons underlined) and the intron sequences surrounding them (bold, not underlined) of the human ABCA4 gene. The sequences of the initially designed 37 AONs (AON1-37; SEQ ID NOs: 1-37, respectively) are shown with their respective complementary positions towards the ABCA4 pre-mRNA. The position of the c.5461-10T>C mutation is given with an arrowhead pointing downwards. Within intron 38 the area that appears to represent a hotspot, where AON1 and 17 bind to as outlined in the examples is given in italic font, which has the sequence of SEQ ID NO: 65. The same holds true for the hotspot in intron 39 where AON12, 31 and 32 bind to, which hotspot has the sequence of SEQ ID NO:66.

FIGS. 3A-3C display SEQ ID NO:44, with the following order of human ABCA4 introns and exons: intron 38 (lower case)—exon 39 (upper case, bold and underlined)—intron 39 (lower case)—exon 40 (upper case, bold and italic)—intron 40 (lower case). Intron 38 (carrying the c.5461-10T>C mutation)=SEQ ID NO:45; Exon 39=SEQ ID NO:46; Intron 39=SEQ ID NO:47; Exon 40=SEQ ID NO:48; Intron 40=SEQ ID NO:49.

FIG. 8 shows the 5' to 3' sequence (SEQ ID NO:67) of the insert in the MG3_2 mini gene construct. EcoRI and SalI sites are at the terminal 5' and 3' ends respectively. Exon 39 (SEQ ID NO:46) of the human ABCA4 gene is in upper case. Intron 38 (SEQ ID NO:45, at the 5' end of exon 39) and intron 39 (SEQ ID NO:47, at the 3' end of exon 39) are underlined. The remainder of the sequences between the EcoRI site and intron 38 on the 5' end of the insert, and the sequences between intron 39 and the SalI site at the 3' end of the insert are identical to what was already present in the backbone plasmid, as described in the examples. RHO exon 3 and RHO exon 5 sequences (SEQ ID NO:68 and SEQ ID NO:69 respectively) are at the 5' side of the ABCA4 intron 38 and 3' side of intron 39 respectively and given in bold.

DETAILED DESCRIPTION

Figure 1:
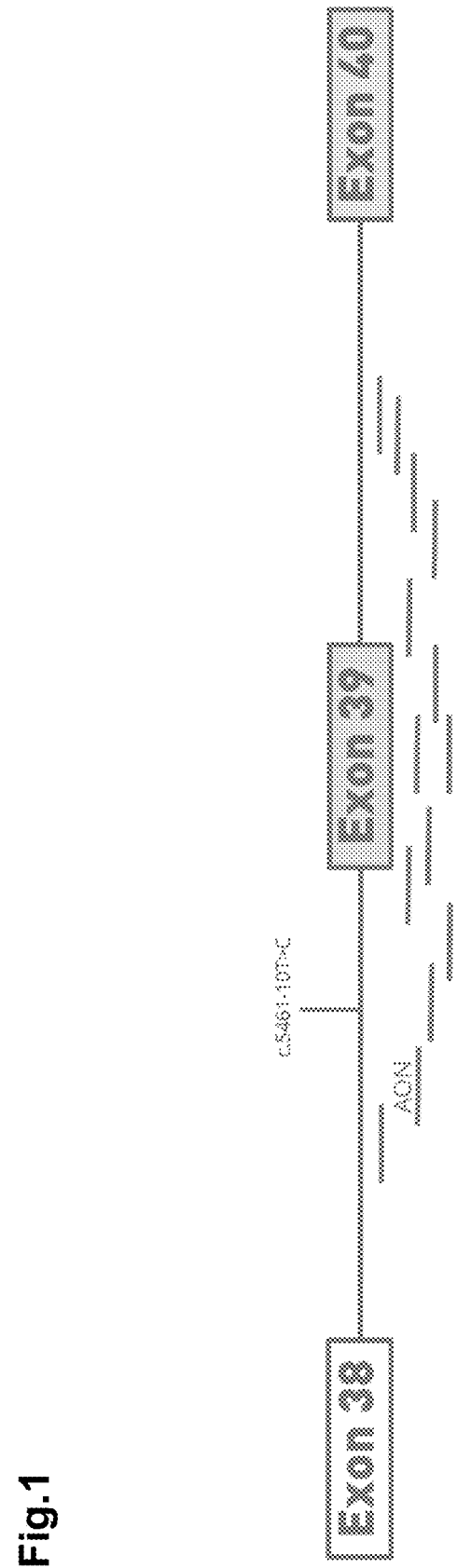
FIG. 1 is a schematic representation of the complementary positions of the tested antisense oligonucleotides (AONs) relative to exon 38, intron 38, exon 39, intron 39 and exon 40 in the human ABCA4 gene. The relative position of the c.5461-10T>C mutation in intron 38 between exon 38 and exon 39 is indicated.

The present invention relates to specific antisense oligonucleotides (AONs) that are able to prevent, inhibit and/or block the skipping of exon 39, or prevent, inhibit and/or block the double skipping of exon 39+exon 40 in the human ABCA4 pre-mRNA. It has been shown that such (double) skipping may at least be caused by the relatively common c.5461-10T>C Stargardt disease causing mutation in intron 38 (Sangermano et al. 2016; Aukrust et al. 2016). Although an AON that induces the skip of exon 10 from human ABCA4 pre-mRNA is known in the art (WO 2015/004133), it was to date unknown whether AONs could also be used for exon retention in the human ABCA4 pre-mRNA, or in other words, for inhibiting exon skipping in human ABCA4 pre-mRNA. The inventors of the present invention hypothesized that such could potentially be possible by identifying particular sequences within the introns and exons surrounding exon 39, and at the intron/exon boundaries, that could then be targeted by purified synthetic antisense oligonucleotides that would be complementary to such sequences and bind thereto under physiological conditions, and that would be able to mask aberrant splice sites and block (to a certain level) or inhibit the splicing of exon 39 (either alone or together with exon 40) from human ABCA4 pre-mRNA. It is known that the skip of exon 39 (either or not together with exon 40) leads to Stargardt disease. The inventors of the present invention envisioned that using antisense oligonucleotides that could prevent (or inhibit to a certain extent) the skipping of exon 39 (either alone or together with exon 40) would enable one to treat, prevent or delay Stargardt disease in human subjects carrying a mutation that causes such exon 39 skipping.

The invention relates to an antisense oligonucleotide (AON) that is able to inhibit skipping of at least one exon in human ABCA4 pre-mRNA, wherein the exon skipping is due to a mutation in the ABCA4 gene. In a preferred embodiment, the mutation causing the exon skipping is in an intron. More preferably, said intronic mutation is the c.5461-10T>C mutation in intron 38 of the human ABCA4 gene. In one preferred embodiment, the AON of the invention is able to inhibit exon 39 skipping and/or exon 39/exon 40 double skipping in human ABCA4 pre-mRNA. In a further preferred embodiment, the AON according to the present invention comprises a sequence that is complementary to at least 8, 9, 10, 11, 12, 13, 14, 15, 16, 17, 18, 19, or 20 consecutive nucleotides within SEQ ID NO:44. Preferably, the AON of the present invention comprises 20, 21, 22, 23, 24 or 25 nucleotides, that are preferably fully complementary to a consecutive sequence within the sequence of SEQ ID NO:44, and further comprises at most one CpG motif. More preferably, there are no CpG motifs in the AON of the invention. In another preferred aspect, the AON according to the invention comprises or consists of a sequence that is complementary to at least 8, 9, 10, 11, 12, 13, 14, 15, 16, 17, 18, 19, 20, 21, 22, 23, 24, or 25 nucleotides within SEQ ID NO:65 or SEQ ID NO:66. Most preferred are AONs that consist of 22, 23, 24, or 25 nucleotides and that are fully complementary to the regions represented by SEQ ID NO:65 or 66. Moreover, it is preferred to keep the percentage of guanosines as low as possible, preferably below 60%, below 50%, below 40%, or even below 30% in the AON of the invention. It is also preferred to keep a stretch of guanosines to a maximum of three and to have at most one stretch of three guanosines in an AON of the invention. In a highly preferred aspect, the AON of the present invention comprises or consists of a sequence of any one of SEQ ID NO:1, 3, 4, 5, 6, 9, 12, 13, 14, 17, 20, 24, 25, 29, 31, and 32, more preferably of SEQ ID NO:1, 3, 4, 6, 12, 17, 24, 25, 29, 31 and 32, even more preferably of SEQ ID NO:1, 12, 17, 24, 29, 31 and 32.

In another preferred aspect, the AON according to the invention is an oligoribonucleotide (RNA oligonucleotide) comprising at least one 2'-O alkyl modification, such as a 2'-O-methyl (2'-OMe) modified sugar. In a further preferred embodiment, all nucleotides in said AON are 2'-O-methyl modified. In another preferred aspect, the AON comprises at least one 2'-O-methoxyethyl (2'-MOE; or 2'-methoxyethoxy) modification. In another aspect 2'-OMe and 2'-MOE modifications may both be present at different nucleosides within the oligonucleotide. Also, AONs according to the invention may be composed of nucleosides that all carry a 2'-OMe modification, or that may be composed of nucleosides that all carry a 2'-MOE modification. In yet another preferred embodiment, the AON according to the present invention comprises at least one phosphorothioate linkage, and more preferably, all sequential nucleotides within the AON are interconnected by phosphorothioate linkages.

The present invention also relates to a pharmaceutical composition comprising an AON according to the invention, and a pharmaceutically acceptable carrier. Preferably, said pharmaceutical composition is for intravitreal administration and is preferably dosed in an amount ranging from 0.05 mg to 5 mg of total AON per eye. The present invention also relates to a pharmaceutical composition according to the invention, wherein the pharmaceutical composition is for intravitreal administration and is dosed in an amount ranging from 0.1 to 1 mg of total AON per eye, such as about 0.1, 0.2, 0.3, 0.4, 0.5, 0.6, 0.7, 0.8, 0.9 or 1.0 mg of total AON per eye. The present invention also relates to a viral vector expressing an AON according to the invention. In yet another aspect, the invention relates to an AON according to the invention, a pharmaceutical composition according to the invention, or a viral vector according to the invention, for use as a medicament. In yet another aspect, the invention relates to an AON according to the invention, a pharmaceutical composition according to the invention, or a viral vector according to the invention, for use in the treatment, prevention or delay of Stargardt disease, or for use in the inhibition of exon 39 skipping in human ABCA4 pre-mRNA. In yet another embodiment, the invention relates to the use of an AON according to the invention, a pharmaceutical composition according to the invention, or a viral vector according to the invention, for the treatment, prevention or delay of Stargardt disease, or for the inhibition of exon 39 skipping in human ABCA4 pre-mRNA. The invention further relates to a method for modulating splicing of ABCA4 pre-mRNA in a cell, said method comprising contacting said cell with an AON according to the invention, a pharmaceutical composition according to the invention, or a viral vector according to the invention. In a preferred aspect the invention relates to a method for the treatment of Stargardt disease or a condition requiring modulating splicing of ABCA4 pre-mRNA of an individual in need thereof, said method comprising contacting a cell of said individual with an AON according to the invention, a pharmaceutical composition according to the invention, or a viral vector according to the invention. The modulation of splicing preferably involves the inhibition of exon 39 skipping that is caused by or is due to a mutation within the human ABCA4 gene, preferably by the c.5461-10T>C mutation in intron 38.

In respect of ABCA4, 'exon retention', or 'inhibiting, blocking or preventing exon skipping', which is the result of the administration/introduction of an AON in a cell, is to be construed as the inclusion (or maintaining the presence) of exon 39, or both exon 39+exon 40 in human ABCA4 pre-mRNA (and subsequent resulting human ABCA4 mRNA). This exon retention, as outlined herein in detail, occurs after administration of an antisense oligonucleotide according to the invention, to the cell, despite the presence of a mutation in the ABCA4 gene that would normally induce skipping of exon 39, or skipping of exon 39 and exon 40, and that may result in Stargardt disease. The term 'exon retention' also refers to inducing, producing or increasing production within a cell of a mature mRNA that does still contain a particular exon or particular exons that should preferably be present in the mature mRNA.

The term 'exon skipping' is herein defined as the appearance of a mature mRNA that does not contain one or more particular exons (in the current case exon 39, or exon 39 together with exon 40 of the ABCA4 gene, which is also referred to as 'double skipping'). These exons would normally be present in the mature mRNA when no exon skipping occurs, such as for instance in a wild type situation. Blocking such exon skipping is achieved by providing a cell expressing the pre-mRNA comprising the Stargardt disease causing variant, with a molecule capable of interfering at sequences such as, for example, the (cryptic) splice donor or (cryptic) splice acceptor sequence required for allowing the enzymatic process of splicing.

The term 'pre-mRNA' refers to a non-processed or partly processed precursor mRNA that is synthesized from a DNA template of a cell by transcription, such as in the nucleus.

The term 'antisense oligonucleotide' (AON) is understood to refer to a nucleotide sequence which is substantially complementary to a target nucleotide sequence in a pre-mRNA molecule, hnRNA (heterogenous nuclear RNA) or mRNA molecule. The degree of complementarity (or substantial complementarity) of the antisense sequence is preferably such that a molecule comprising the antisense sequence can form a stable double stranded hybrid with the target nucleotide sequence in the RNA molecule under physiological conditions. The terms 'antisense oligonucleotide', 'oligonucleotide' and 'oligo' are used interchangeably herein and are understood to refer to an oligonucleotide comprising an antisense sequence in respect of the target (pre-) mRNA sequence.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

The word "about" or "approximately" when used in association with a numerical value (e.g. about 10) preferably means that the value may be the given value (of 10) more or less 0.1% of the value.

In one embodiment, an exon 39 retention molecule (or an exon 39/40 retention molecule) as defined herein is an AON that binds and/or is complementary to a specified sequence, preferably a sequence within SEQ ID NO:44, and causes the retention of exon 39, or exon 39+exon 40 in the ABCA4 mRNA. Binding to one of the specified target sequences, preferably in the context of the aberrant ABCA4 may be assessed via techniques known to the skilled person. A preferred technique is gel mobility shift assay as described in EP1619249. In a preferred embodiment, an exon 39 retention AON (or an exon 39/40 retention AON) is said to bind to one of the specified sequences as soon as a binding of said molecule to a labeled target sequence is detectable in a gel mobility shift assay.

In all embodiments of the invention, an exon 39 retention molecule (or an exon 39/40 retention molecule) is preferably an AON. Preferably, an exon 39 retention AON (or an exon 39/40 retention AON) according to the invention is an AON, which is complementary or substantially complementary to a sequence within intron 38, exon 39, intron 39, exon 40, or intron 40 of the human ABCA4 pre-mRNA, or to sequences that overlap with the boundaries of intron 38/exon 39, exon 39/intron 39, intron 39/exon 40, or exon 40/intron 40 of the human ABCA4 pre-mRNA. More preferably, an AON of the present invention comprises a nucleotide sequence of any one of the sequences of SEQ ID NO:1 to 37.

The term 'substantially complementary' used in the context of the invention indicates that some mismatches in the antisense sequence are allowed as long as the functionality, i.e. blocking skipping of the ABCA4 exon 39, or blocking skipping of exon 39+exon 40 is still acceptable. Preferably, the complementarity is from 90% to 100%. In general this allows for 1 or 2 mismatches in an AON of 20 nucleotides or 1, 2, 3 or 4 mismatches in an AON of 40 nucleotides, or 1, 2, 3, 4, 5, or 6 mismatches in an AON of 60 nucleotides, etc.

The invention also provides a method for designing an AON that is able to inhibit or block skipping of the ABCA4 exon 39, or is able to inhibit or block the skipping of ABCA4 exon 39 together with exon 40. First, said AON is selected to bind to (under physiological conditions) and/or to be complementary to a sequence within intron 38, exon 39, intron 39, exon 40, or intron 40 of the human ABCA4 pre-mRNA, or to sequences that overlap with the boundaries of intron 38/exon 39, exon 39/intron 39, intron 39/exon 40, or exon 40/intron 40 of the human ABCA4 pre-mRNA. Subsequently, in a preferred method at least one of the following aspects has to be taken into account for designing, improving said exon retention AON further: the exon retention AON of the present invention preferably contains at most one CpG motif, and more preferably does not contain a CpG motif at all. The presence of a CpG motif or a multiplicity of CpG motifs (CpG islands) in an AON is usually associated with an increased immunogenicity of said AON (Dorn and Kippenberger (2008) Curr Opin Mol Ther 10(1) 10-20). This increased immunogenicity is undesired since it may induce damage of the tissue to be treated, i.e. the eye. Immunogenicity may be assessed in an animal model by assessing the presence of CD4+ and/or CD8+ cells and/or inflammatory mononucleocyte infiltration. Immunogenicity may also be assessed in blood of an animal or of a human being treated with an AON of the invention by detecting the presence of a neutralizing antibody and/or an antibody recognizing said AON using a standard immunoassay known to the skilled person. An inflammatory reaction, type I-like interferon production, IL-12 production and/or an increase in immunogenicity may be assessed by detecting the presence or an increasing amount of a neutralizing antibody or an antibody recognizing said AON using a standard immunoassay.

The invention allows designing an AON with acceptable RNA binding kinetics and/or thermodynamic properties. The RNA binding kinetics and/or thermodynamic properties are at least in part determined by the melting temperature of an AON (Tm; calculated with a oligonucleotide properties calculator known to the person skilled in the art, for single stranded RNA using the basic Tm and the nearest neighbor model), and/or the free energy of the AON-target exon complex (using RNA structure version 4.5). If a Tm is too high, the AON is expected to be less specific. An acceptable Tm and free energy depend on the sequence of the AON. Therefore, it is difficult to give preferred ranges for each of these parameters. An acceptable Tm may be ranged between 35 and 70° C. and an acceptable free energy may be ranged between 15 and 45 kcal/mol.

Figure 6:
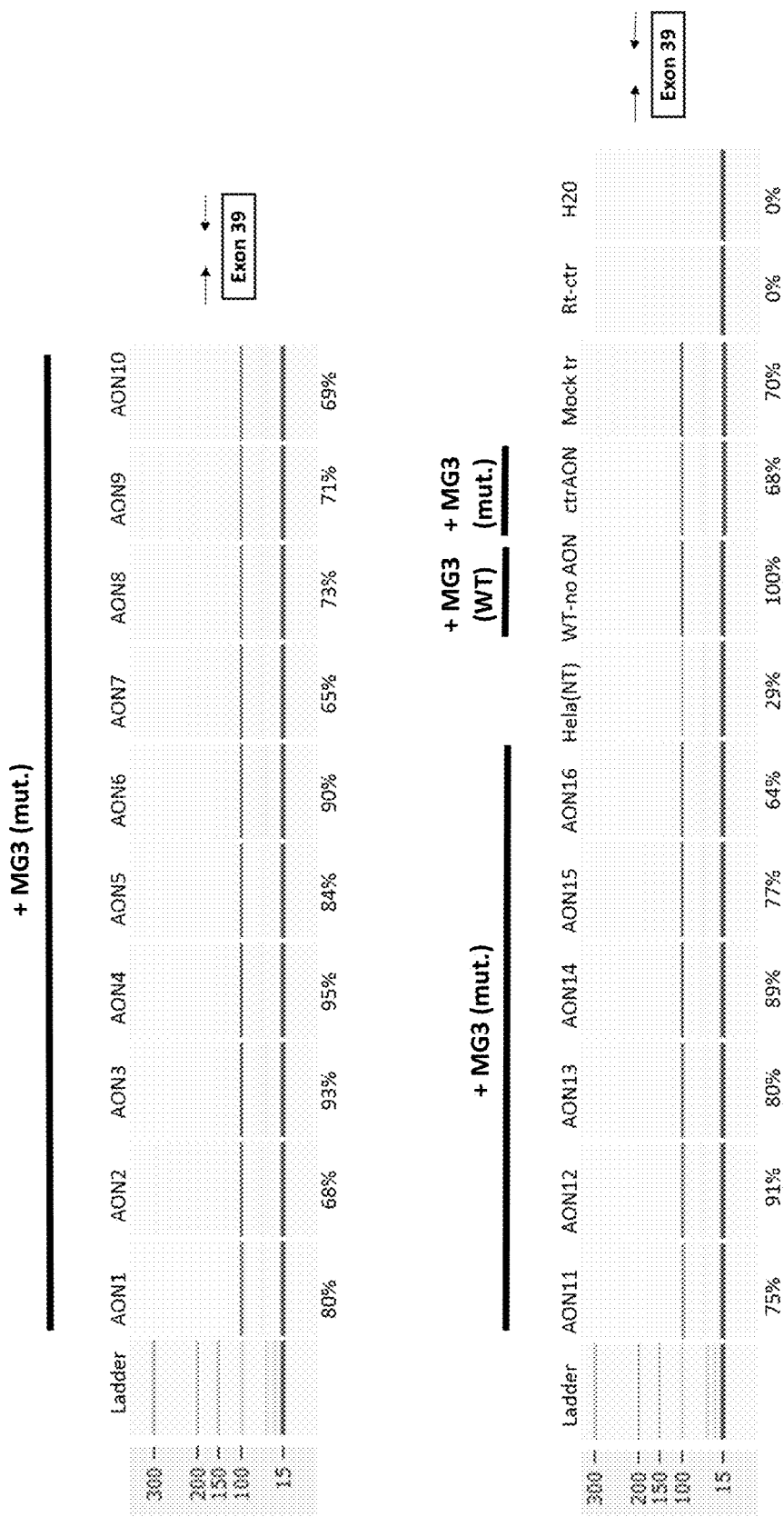
FIG. 6 shows the RT-PCR results on a Bioanalyzer after transfection of HeLa cells with MG3 carrying the c.5461-10T mutation (+MG3 mut.) and MG3 wild type (MG3 WT) constructs, with and without different AONs. Initially the sixteen AONs of SEQ ID NO:1 to 16 were tested on the mutant version. The RT-PCR was performed with primers annealing within the exon 39 sequence, which makes that the lane indicated with "HeLa(NT)" (non-transfected HeLa cells) in the lower panel also shows a band at the expected level. This is due to the fact that HeLa cells carry the wild type ABCA4 gene, from which apparently also a PCR product was generated. The negative control ("ctrAON") was a transfection with the MG3 construct harboring the mutation and an unrelated AON. Another negative control is the "Mock tr" lane that represents cells that were transfected only with the transfection reagents, not with constructs or AON. "Rt-ctr" and "H$_2$O" were two additional negative controls for the PCR reaction, without cell material. An increase in intensity of the product band suggests an increase of mRNA comprising exon 39. Because such should be assessed based on what is already generated in HeLa cells as a background, and in fact relative to the WT signal wherein no AON is transfected, the lane indicated with "WT-no AON" was taken as 100% and the Bioanalyzer software was applied to measure the intensity of the other bands in comparison to that 100% intensity. This shows that approximately ⅓ of that signal (29%) may be due to the background HeLa alone signal. It also shows that transfection itself with or without AON is able to give an AON-unrelated boost of the signal to around 70%. However, the intensity detected with AON1, AON3, AON4, AON5, AON6, AON12, AON13, and AON14 was increased to at least 80%, with AON3, AON4, AON6, and AON12 performing best, with intensities of at least 90% of the WT signal, set at 100%. This shows that these AONs were able to block exon 39 skipping from the MG3 mutation construct to levels that are close to wild type in which exon 39 is not skipped.

An AON of the invention is preferably one that is able to exhibit an acceptable level of functional activity. A functional activity of said AON is preferably to block the skipping of exon 39, or exon 39+exon 40 of ABCA4 pre-mRNA to a certain acceptable level, to provide an individual with a certain detectable level of functional wild type and full length ABCA4 protein. In a preferred embodiment, an AON is said to block skipping of the ABCA4 exon 39, or the ABCA4 exon 39+exon 40, when the full length mRNA, including the exons as measured by RT-PCR and/or ddPCR analysis is at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100% as compared to a control wt RNA product, in the absence of a background signal. As is seen in FIG. 6, the percentage range of retention (as outlined above) is dependent on the background signal, which should preferably be absent. Hence, such percentages are preferably measured in a system or by using PCR primers that do not give a background signal. The aim of the present invention is to provide AONs that block or prevent exon 39/40 skipping in ABCA4 pre-mRNA. Assays to determine exon skipping and/or exon retention are described in the examples herein and may be supplemented with techniques known to the person skilled in the art to judge whether an increased exon 39 retention is found.

Preferably, an AON according to the invention comprises a sequence that is complementary or substantially complementary to SEQ ID NO:65, SEQ ID NO:66, a nucleotide sequence of intron 38 (SEQ ID NO:45), exon 39 (SEQ ID NO:46), intron 39 (SEQ ID NO:47), exon 40 (SEQ ID NO:48), or intron 40 (SEQ ID NO:49) of the human ABCA4 pre-mRNA (as given in full in SEQ ID NO:44, carrying the c.5461-10T>C mutation), or to sequences that overlap with the boundaries of intron 38/exon 39, exon 39/intron 39, intron 39/exon 40, or exon 40/intron 40 of the human ABCA4 pre-mRNA, and is such that the (substantially) complementary part is at least 50% of the length of the AON according to the invention, more preferably at least 60%, even more preferably at least 70%, even more preferably at least 80%, even more preferably at least 90% or even more preferably at least 95%, or even more preferably 98% or even more preferably at least 99%, or even more preferably 100%. More preferably, the AON is complementary to a sequence that includes the boundary between intron 38 and exon 39, and even more preferably includes the c.5461-10T>C mutation. In another aspect of the invention, an AON according to the invention comprises or consists of a sequence of SEQ ID NO:1 to 16, more preferably comprises or consists of a sequence selected from the group consisting of SEQ ID NO:1, 3, 4, 5, 6, 9, 12, 13, 14, 17, 20, 24, 25, 29, 31 and 32, preferably SEQ ID NO:1, 12, 17, 24, 29, 31 and 32.

In another preferred embodiment, the length of the complementary part of the AON of the present invention is at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides. Additional flanking sequences may be used to modify the binding of a protein to the AON, or to modify a thermodynamic property of the AON, more preferably to modify target RNA binding affinity.

It is thus not absolutely required that all the bases in the region of complementarity are capable of pairing with bases in the opposing strand. For instance, when designing the AON one may want to incorporate for instance a residue that does not base pair with the base on the complementary strand. Mismatches may, to some extent, be allowed, if under the circumstances in the cell, the stretch of nucleotides is sufficiently capable of hybridizing to the complementary part. In this context, 'sufficiently' preferably means that using a gel mobility shift assay as described in example 1 of EP1619249, binding of an AON is detectable.

Optionally, said AON may further be tested by using optic cups (or eye cups) generated from fibroblasts derived from Stargardt disease patients, using methods known to the person skilled in the art. Blocking the skip of exon 39/40 may be assessed by RT-PCR (along the lines as described in Aukrust et al. 2016). The complementary regions are preferably designed such that, when combined, they are specific for the exon in the pre-mRNA. Such specificity may be created with various lengths of complementary regions as this depends on the actual sequences in other (pre-)mRNA molecules in the system. The risk that the AON also will be able to hybridize to one or more other pre-mRNA molecules decreases with increasing size of the AON. It is clear that AONs comprising mismatches in the region of complementarity but that retain the capacity to hybridize and/or bind to the targeted region(s) in the pre-mRNA, can be used in the invention. However, preferably at least the complementary parts do not comprise such mismatches as AONs lacking mismatches in the complementary part typically have a higher efficiency and a higher specificity, than AONs having such mismatches in one or more complementary regions. It is thought that higher hybridization strengths (i.e. increasing number of interactions with the opposing strand) are favorable in increasing the efficiency of the process of interfering with the splicing machinery of the system. Preferably, the complementarity is from 90% to 100%. In general this allows for 1 or 2 mismatches in an AON of 20 nucleotides or 1, 2, 3, or 4 mismatches in an AON of 40 nucleotides, or 1, 2, 3, 4, 5, or 6 mismatches in an AON of 60 nucleotides, etc.

An AON of the invention is preferably an isolated single stranded molecule in the absence of its (target) counterpart sequence, and that does not self-hybridize. An AON of the invention is preferably complementary to, or under physiological conditions binds to a sequence of intron 38, exon 39, intron 39, exon 40, or intron 40 of the human ABCA4 pre-mRNA, or to a sequence that overlaps with the boundaries of intron 38/exon 39, exon 39/intron 39, intron 39/exon 40, or exon 40/intron 40 of the human ABCA4 pre-mRNA.

A preferred AON of the invention comprises or consists of from 8 to 143 nucleotides, more preferably from 10 to 40 nucleotides, more preferably from 12 to 30 nucleotides, more preferably from 20 to 30 nucleotides, and preferably comprises or consists of 8, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides. More preferably, the AON according to the present invention comprises or consists of 20, 21, 22, 23, 24 or 25 nucleotides.

In certain embodiments, the invention provides a single stranded AON selected from the group consisting of SEQ ID NO:1 to 37. An AON according to the invention may contain one of more RNA residues, or one or more DNA residues, and/or one or more nucleotide analogues or equivalents, as will be further detailed herein below. It is preferred that an AON of the invention comprises one or more residues that are modified to increase nuclease resistance, and/or to increase the affinity of the AON for the target sequence. Therefore, in a preferred embodiment, the AON sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells. A recent report demonstrated triplex formation by a morpholino oligonucleotide and, because of the non-ionic backbone, these studies showed that the morpholino oligonucleotide was capable of triplex formation in the absence of magnesium.

It is further preferred that the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) *Science* 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) *Chem Commun* 495-497). Since the backbone of a PNA molecule contains no charged phosphate groups, PNA-RNA hybrids are usually more stable than RNA-RNA or RNA-DNA hybrids, respectively (Egholm et al. (1993) *Nature* 365:566-568). A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; dimethylamino oxyethoxy; and -dimethylaminoethoxyethoxy. The sugar moiety can be a pyranose or derivative thereof, or a deoxypyranose or derivative thereof, preferably ribose or derivative thereof, or deoxyribose or derivative thereof. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-O, 4'-C-ethylene-bridged nucleic acid (Morita et al. 2001. *Nucleic Acid Res Supplement No.* 1:241-242). These substitutions render the nucleotide analogue or equivalent RNase H and nuclease resistant and increase the affinity for the target RNA.

In another embodiment, a nucleotide analogue or equivalent of the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an AON to be modified uniformly. In addition, more than one of the aforementioned analogues or equivalents may be incorporated in a single AON or even at a single position within an AON. In certain embodiments, an AON of the invention has at least two different types of analogues or equivalents. A preferred exon skipping AON according to the invention comprises a 2'-O alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives. An effective AON according to the invention comprises a 2'-O-methyl ribose with a (preferably full) phosphorothioate backbone.

It will also be understood by a skilled person that different AONs can be combined for efficiently blocking the skip of exons 39 and 40 in the ABCA4 pre-mRNA. In a preferred embodiment, a combination of at least two AONs are used in a method of the invention, such as 2, 3, 4, or 5 different AONs. Hence, the invention also relates to a set of AONs comprising at least one AON according to the present invention.

As indicated above, the presence of the c.5461-10T>C mutation in intron 38 of the ABCA4 gene induces skipping of exon 39 and often co-skipping of exon 40. Hence, it is preferred to use an AON that efficiently blocks exon 39 skipping while also retaining exon 40.

An AON can be linked to a moiety that enhances uptake of the AON in cells, preferably retina cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a cameloid single domain antigen-binding domain.

An AON according to the invention may be indirectly administrated using suitable means known in the art. It may for example be provided to an individual or a cell, tissue or organ of said individual in the form of an expression vector wherein the expression vector encodes a transcript comprising said oligonucleotide. The expression vector is preferably introduced into a cell, tissue, organ or individual via a gene delivery vehicle. In a preferred embodiment, there is provided a viral-based expression vector comprising an expression cassette or a transcription cassette that drives expression or transcription of an AON as identified herein. Accordingly, the invention provides a viral vector expressing an AON according to the invention when placed under conditions conducive to expression of the AON. Expression may be driven by a polymerase II-promoter (Pol II) such as a U7 promoter or a polymerase III (Pol III) promoter, such as a U6 RNA promoter. A preferred delivery vehicle is a viral vector such as an adeno associated virus vector (AAV), or a retroviral vector such as a lentivirus vector and the like. Also, plasmids, artificial chromosomes, plasmids usable for targeted homologous recombination and integration in the human genome of cells may be suitably applied for delivery of an oligonucleotide as defined herein. Preferred for the current invention are those vectors wherein transcription is driven from Pol III promoters, and/or wherein transcripts are in the form fusions with U1 or U7 transcripts, which yield good results for delivering small transcripts. It is within the skill of the artisan to design suitable transcripts. Preferred are Pol III driven transcripts, preferably, in the form of a fusion transcript with an U1 or U7 transcript. Such fusions may be generated as described (Gorman et al. 1998. Stable alteration of pre-mRNA splicing patterns by modified U7 small nuclear RNAs. *Proc Natl Acad Sci USA* 95(9):4929-34; Suter et al. 1999. Double-target antisense U7 snRNAs promote efficient skipping of an aberrant exon in three human beta-thalassemic mutations. *Hum Mol Genet* 8(13): 2415-23).

The AON of the present invention may be delivered as such (naked). However, an AON of the present invention may also be encoded by a viral vector. Typically, this is in the form of an RNA transcript that comprises the sequence of an oligonucleotide according to the invention in a part of the transcript. An AAV vector according to the invention is a recombinant AAV vector and refers to an AAV vector comprising part of an AAV genome comprising an encoded AON according to the invention encapsidated in a protein shell of capsid protein derived from an AAV serotype as depicted elsewhere herein. Part of an AAV genome may contain the inverted terminal repeats (ITR) derived from an adeno-associated virus serotype, such as AAV1, AAV2, AAV3, AAV4, AAV5, AAV8, AAV9 and others. Protein shell comprised of capsid protein may be derived from an AAV serotype such as AAV1, 2, 3, 4, 5, 8, 9 and others. A protein shell may also be named a capsid protein shell. AAV vector may have one or preferably all wild type AAV genes deleted, but may still comprise functional ITR nucleic acid sequences. Functional ITR sequences are necessary for the replication, rescue and packaging of AAV virions. The ITR sequences may be wild type sequences or may have at least 80%, 85%, 90%, 95, or 100% sequence identity with wild type sequences or may be altered by for example in insertion, mutation, deletion or substitution of nucleotides, as long as they remain functional. In this context, functionality refers to the ability to direct packaging of the genome into the capsid shell and then allow for expression in the host cell to be infected or target cell. In the context of the invention a capsid protein shell may be of a different serotype than the AAV vector genome ITR. An AAV vector according to present the invention may thus be composed of a capsid protein shell, i.e. the icosahedral capsid, which comprises capsid proteins (VP1, VP2, and/or VP3) of one AAV serotype, e.g. AAV serotype 2, whereas the ITRs sequences contained in that AAV5 vector may be any of the AAV serotypes described above, including an AAV2 vector. An "AAV2 vector" thus comprises a capsid protein shell of AAV serotype 2, while e.g. an "AAV5 vector" comprises a capsid protein shell of AAV serotype 5, whereby either may encapsidate any AAV vector genome ITR according to the invention. Preferably, a recombinant AAV vector according to the invention comprises a capsid protein shell of AAV serotype 2, 5, 8 or AAV serotype 9 wherein the AAV genome or ITRs present in said AAV vector are derived from AAV serotype 2, 5, 8 or AAV serotype 9; such AAV vector is referred to as an AAV2/2, AAV 2/5, AAV2/8, AAV2/9, AAV5/2, AAV5/5, AAV5/8, AAV 5/9, AAV8/2, AAV 8/5, AAV8/8, AAV8/9, AAV9/2, AAV9/5, AAV9/8, or an AAV9/9 vector.

More preferably, a recombinant AAV vector according to the invention comprises a capsid protein shell of AAV serotype 2 and the AAV genome or ITRs present in said vector are derived from AAV serotype 5; such vector is referred to as an AAV 2/5 vector. More preferably, a recombinant AAV vector according to the invention comprises a capsid protein shell of AAV serotype 2 and the AAV genome or ITRs present in said vector are derived from AAV serotype 8; such vector is referred to as an AAV 2/8 vector. More preferably, a recombinant AAV vector according to the invention comprises a capsid protein shell of AAV serotype 2 and the AAV genome or ITRs present in said vector are derived from AAV serotype 9; such vector is referred to as an AAV 2/9 vector. More preferably, a recombinant AAV vector according to the invention comprises a capsid protein shell of AAV serotype 2 and the AAV genome or ITRs present in said vector are derived from AAV serotype 2; such vector is referred to as an AAV 2/2 vector. A nucleic acid molecule encoding an exon 39 retention AON (or exon 39/exon 40 retention AON) according to the invention represented by a nucleic acid sequence of choice is preferably inserted between the AAV genome or ITR sequences as identified above, for example an expression construct comprising an expression regulatory element operably linked to a coding sequence and a 3' termination sequence. "AAV helper functions" generally refers to the corresponding AAV functions required for AAV replication and packaging supplied to the AAV vector in trans. AAV helper functions complement the AAV functions which are missing in the AAV vector, but they lack AAV ITRs (which are provided by the AAV vector genome). AAV helper functions include the two major ORFs of AAV, namely the rep coding region and the cap coding region or functional substantially identical sequences thereof. Rep and Cap regions are well known in the art. The AAV helper functions can be supplied on an AAV helper construct, which may be a plasmid.

Introduction of the helper construct into the host cell can occur e.g. by transformation, transfection, or transduction prior to or concurrently with the introduction of the AAV genome present in the AAV vector as identified herein. The AAV helper constructs of the invention may thus be chosen such that they produce the desired combination of serotypes for the AAV vector's capsid protein shell on the one hand and for the AAV genome present in said AAV vector replication and packaging on the other hand. "AAV helper virus" provides additional functions required for AAV replication and packaging.

Suitable AAV helper viruses include adenoviruses, herpes simplex viruses (such as HSV types 1 and 2) and vaccinia viruses. The additional functions provided by the helper virus can also be introduced into the host cell via vectors, as described in U.S. Pat. No. 6,531,456 incorporated herein by reference. Preferably, an AAV genome as present in a recombinant AAV vector according to the invention does not comprise any nucleotide sequences encoding viral proteins, such as the rep (replication) or cap (capsid) genes of AAV.

An AAV genome may further comprise a marker or reporter gene, such as a gene for example encoding an antibiotic resistance gene, a fluorescent protein (e.g. gfp) or a gene encoding a chemically, enzymatically or otherwise detectable and/or selectable product (e.g. lacZ, aph, etc.) known in the art. Preferably, an AAV vector according to the invention is constructed and produced according to the methods in the Examples herein. A preferred AAV vector according to the invention is an AAV vector, preferably an AAV2/5, AAV2/8, AAV2/9 or AAV2/2 vector, expressing an AON according to the invention that comprises, or preferably consists of, a sequence that is complementary or substantially complementary to a nucleotide sequence of intron 38, exon 39, intron 39, exon 40, or intron 40 of the human ABCA4 pre-mRNA, or a sequence that overlaps with the boundaries of intron 38/exon 39, exon 39/intron 39, intron 39/exon 40, or exon 40/intron 40 of the human ABCA4 pre-mRNA. A further preferred AAV vector according to the invention is an AAV vector, preferably an AAV2/5, AAV2/8, AAV2/9 or AAV2/2 vector, expressing an AON according to the invention that comprises, or preferably consists of any one of SEQ ID NO:1 to 37.

Improvements in means for providing an individual or a cell, tissue, organ of said individual with an AON according to the invention, are anticipated considering the progress that has already thus far been achieved. Such future improvements may of course be incorporated to achieve the mentioned effect on restructuring of mRNA using a method of the invention. An AON according to the invention can be delivered as is to an individual, a cell, tissue or organ of said individual. When administering an AON according to the invention, it is preferred that the AON is dissolved in a solution that is compatible with the delivery method. Retina cells can be provided with a plasmid for AON expression by providing the plasmid in an aqueous solution. Alternatively, a preferred delivery method for an AON or a plasmid for AON expression is a viral vector or nanoparticles. Preferably viral vectors or nanoparticles are delivered to retina cells. Such delivery to retina cells or other relevant cells may be in vivo, in vitro or ex vivo. Nanoparticles and microparticles that may be used for in vivo AON delivery are well known in the art. Alternatively, a plasmid can be provided by transfection using known transfection reagents. For intravenous, subcutaneous, intramuscular, intrathecal and/or intraventricular administration it is preferred that the solution is a physiological salt solution. Particularly preferred in the invention is the use of an excipient or transfection reagents that will aid in delivery of each of the constituents as defined herein to a cell and/or into a cell (preferably a retina cell). Preferred are excipients or transfection reagents capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients or transfection reagents comprise polyethylenimine (PEI; ExGen500 (MBI Fermentas)), LipofectAMINE™ 2000 (Invitrogen) or derivatives thereof, or similar cationic polymers, including polypropyleneimine or polyethylenimine copolymers (PECs) and derivatives, synthetic amphiphils (SAINT-18), Lipofectin™, DOTAP and/or viral capsid proteins that are capable of self-assembly into particles that can deliver each constituent as defined herein to a cell, preferably a retina cell. Such excipients have been shown to efficiently deliver an AON to a wide variety of cultured cells, including retina cells. Their high transfection potential is combined with an excepted low to moderate toxicity in terms of overall cell survival. The ease of structural modification can be used to allow further modifications and the analysis of their further (in vivo) nucleic acid transfer characteristics and toxicity. Lipofectin represents an example of a liposomal transfection agent. It consists of two lipid components, a cationic lipid N-[1-(2,3 dioleoyloxy)propyl]-N, N, N-trimethylammonium chloride (DOTMA) (cp. DOTAP which is the methylsulfate salt) and a neutral lipid dioleoylphosphatidyl ethanolamine (DOPE). The neutral component mediates the intracellular release. Another group of delivery systems are polymeric nanoparticles. Polycations such as diethylamino ethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver AONs across cell membranes into cells. In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an AON. The skilled person may select and adapt any of the above or other commercially available alternative excipients and delivery systems to package and deliver an AON for use in the current invention to deliver it for the prevention, treatment or delay of an ABCA4-variant related disease or condition. "Prevention, treatment or delay of an ABCA4-variant related disease or condition" is herein preferably defined as preventing, halting, ceasing the progression of, or reversing partial or complete visual impairment or blindness, caused by a genetic defect in the ABCA4 gene.

In addition, an AON according to the invention could be covalently or non-covalently linked to a targeting ligand specifically designed to facilitate the uptake into the cell, cytoplasm and/or its nucleus. Such ligand could comprise (i) a compound (including but not limited to peptide(-like) structures) recognizing cell, tissue or organ specific elements facilitating cellular uptake and/or (ii) a chemical compound able to facilitate the uptake in to cells and/or the intracellular release of an oligonucleotide from vesicles, e.g. endosomes or lysosomes. Therefore, in a preferred embodiment, an AON according to the invention is formulated in a composition or a medicament or a composition, which is provided with at least an excipient and/or a targeting ligand for delivery and/or a delivery device thereof to a cell and/or enhancing its intracellular delivery.

It is to be understood that if a composition comprises an additional constituent such as an adjunct compound as later defined herein, each constituent of the composition may not be formulated in one single combination or composition or preparation. Depending on their identity, the skilled person will know which type of formulation is the most appropriate for each constituent as defined herein. In a preferred embodiment, the invention provides a composition or a preparation which is in the form of a kit of parts comprising an AON according to the invention and a further adjunct compound as later defined herein. If required, an AON according to the invention or a vector, preferably a viral vector, expressing an AON according to the invention can be incorporated into a pharmaceutically active mixture by adding a pharmaceutically acceptable carrier. Accordingly, the invention also provides a composition, preferably a pharmaceutical composition, comprising an AON according to the invention, or a viral vector according to the invention and a pharmaceutically acceptable excipient. Such a pharmaceutical composition may comprise any pharmaceutically acceptable excipient, including a carrier, filler, preservative, adjuvant, solubilizer and/or diluent. Such pharmaceutically acceptable carrier, filler, preservative, adjuvant, solubilizer and/or diluent may for instance be found in Remington (Remington. 2000. The Science and Practice of Pharmacy, 20th Edition. Baltimore, MD: Lippincott Williams Wilkins). Each feature of said composition has earlier been defined herein.

A preferred route of administration is through intra-vitreal injection of an aqueous solution or specially adapted formulation for intraocular administration. EP 2425814 discloses an oil in water emulsion especially adapted for intraocular (intravitreal) administration of peptide or nucleic acid drugs. This emulsion is less dense than the vitreous fluid, so that the emulsion floats on top of the vitreous, avoiding that the injected drug impairs vision.

If multiple distinct AONs according to the invention are used, concentration or dose defined herein may refer to the total concentration or dose of all AONs used or the concentration or dose of each AONs used or added. Therefore in one embodiment, there is provided a composition wherein each or the total amount of AONs according to the invention used is dosed in an amount ranged from 0.01 and 20 mg/kg, preferably from 0.05 and 20 mg/kg. A suitable intravitreal dose would be between 0.05 mg and 5 mg, preferably between 0.1 and 1 mg per eye, such as about per eye: 0.1, 0.2, 0.3, 0.4, 0.5, 0.6, 0.7, 0.8, 0.9 or 1.0 mg.

A preferred AON according to the invention is for the treatment of an ABCA4-variant related disease or condition of an individual. Preferably said ABCA4 variant is the c.5461-10T>C variant, although it cannot be excluded that other ABCA4 mutations may also cause the skipping of exon 39 or exon 39/40, which therefore may also be blocked by an AON of the present invention. Hence, although the AON of the present invention is preferably used in Stargardt disease, which is caused by the known c.5461-10T>C mutation it may also be used for any disease that is caused by the skip of exon 39, or exon 39/40 of the ABCA4 pre-mRNA, which skip results in reduction of (functional) ABCA4 protein. It has now been elucidated that this particular mutation causes that splice effect, but in view of the enormous range of ABCA4 mutations, it cannot be excluded that other mutations also cause the same splicing alteration, which may also be prevented by an AON of the present invention. Hence, the present invention relates to an AON that blocks or prevents the skipping of exon 39 from ABCA4 pre-mRNA, which skip may be caused by the c.5461-10T>C mutation or another (yet unknown) mutation in the ABCA4 gene.

In all embodiments of the invention, the term 'treatment' is understood to include also the prevention and/or delay of the ABCA4-variant related disease or condition. An individual, which may be treated using an AON according to the invention may already have been diagnosed as having an ABCA4-variant related disease or condition. Alternatively, an individual which may be treated using an AON according to the invention may not have yet been diagnosed as having an ABCA4-variant related disease or condition such as Stargardt disease, but may be an individual having an increased risk of developing such disease or condition in the future given his or her genetic background. A preferred individual is a human individual. In a preferred embodiment the ABCA4-variant related disease or condition is Stargardt disease. Accordingly, the invention further provides an AON according to the invention, or a viral vector according to the invention, or a composition according to the invention for use as a medicament, for treating an ABCA4-variant related disease or condition requiring modulating splicing of ABCA4 and for use as a medicament for the prevention, treatment or delay of an ABCA4-variant related disease or condition. Each feature of said use has earlier been defined herein.

The invention further provides the use of an AON according to the invention, or of a viral vector according to the invention, or a composition according to the invention for the treatment of an ABCA4-variant related disease or condition requiring modulating splicing of ABCA4 pre-mRNA. In a preferred embodiment, and for all aspects of the invention, the ABCA4-variant related disorder, disease or condition is caused by the c.5461-10T>C mutation in exon 38 of the human ABCA4 gene.

The invention further provides the use of an AON according to the invention, or of a viral vector according to the invention, or a composition according to the invention for the preparation of a medicament, for the preparation of a medicament for treating an ABCA4-variant related disease or condition requiring modulating splicing of ABCA4 pre-mRNA and for the preparation of a medicament for the prevention, treatment or delay of an ABCA4-variant related disease or condition. Therefore in a further aspect, there is provided the use of an AON, viral vector or composition as defined herein for the preparation of a medicament, for the preparation of a medicament for treating a condition requiring modulating splicing of ABCA4 pre-mRNA and for the preparation of a medicament for the prevention, treatment or delay of an ABCA4-variant related disease or condition.

A treatment in a use or in a method according to the invention is at least once, lasts one week, one month, several months, 1, 2, 3, 4, 5, 6 years or longer, such as lifelong. Each AON or equivalent thereof as defined herein for use according to the invention may be suitable for direct administration to a cell, tissue and/or an organ in vivo of individuals already affected or at risk of developing ABCA4-variant related disease or condition, and may be administered directly in vivo, ex vivo or in vitro. The frequency of administration of an AON, composition, compound or adjunct compound of the invention may depend on several parameters such as the severity of the disease, the age of the patient, the mutation of the patient, the number of AONs (i.e. dose), the formulation of said AON, the route of administration and so forth. The frequency may vary between daily, weekly, at least once in two weeks, or three weeks or four weeks or five weeks or a longer time period. Dose ranges of an AON according to the invention are preferably designed on the basis of rising dose studies in clinical trials (in vivo use) for which rigorous protocol requirements exist. An AON as defined herein, may be used at a dose which is ranged from 0.01 and 20 mg/kg, preferably from 0.05 and 20 mg/kg. A suitable intravitreal dose would be between 0.05 mg and 5 mg, preferably between 0.1 and 1 mg per eye, such as about per eye: 0.1, 0.2, 0.3, 0.4, 0.5, 0.6, 0.7, 0.8, 0.9 or 1.0 mg. In a preferred embodiment, a concentration of an AON as defined herein, which is ranged from 0.1 nM and 1 µM is used. Preferably, this range is for in vitro use in a cellular model such as retina cells or retinal tissue. More preferably, the concentration used is ranged from 1 to 400 nM, even more preferably from 10 to 200 nM, even more preferably from 50 to 100 nM. If several AONs are used, this concentration or dose may refer to the total concentration or dose of AONs or the concentration or dose of each AON added. In a preferred embodiment, a viral vector, preferably an AAV vector as described earlier herein, as delivery vehicle for a molecule according to the invention, is administered in a dose ranging from $1\times10^9$ to $1\times10^{17}$ virus particles per injection, more preferably from $1\times10^{10}$ to $1\times10^{12}$ virus particles per injection. The ranges of concentration or dose of AONs as given above are preferred concentrations or doses for in vivo, in vitro or ex vivo uses. The skilled person will understand that depending on the AONs used, the target cell to be treated, the gene target and its expression levels, the medium used and the transfection and incubation conditions, the concentration or dose of AONs used may further vary and may need to be optimized any further.

An AON according to the invention, or a viral vector according to the invention, or a composition according to the invention for use according to the invention may be suitable for administration to a cell, tissue and/or an organ in vivo of individuals already affected or at risk of developing an ABCA4-variant related disease or condition, and may be administered in vivo, ex vivo or in vitro. Said AON according to the invention, or viral vector according to the invention, or composition according to the invention may be directly or indirectly administered to a cell, tissue and/or an organ in vivo of an individual already affected by or at risk of the disease or condition, and may be administered directly or indirectly in vivo, ex vivo or in vitro. As Stargardt disease has a pronounced phenotype in retina, it is preferred that the cells are retina cells, and it is further preferred that said tissue is the retina and/or it is further preferred that said organ is the eye.

The invention further provides a method for modulating splicing of ABCA4 pre-mRNA in a cell comprising contacting the cell, preferably a retina cell, with an AON according to the invention (hence, an AON that blocks skipping of exon 39), or a viral vector according to the invention, or a composition according to the invention. The features of this aspect are preferably those defined earlier herein. Contacting the cell with an AON according to the invention, or a viral vector according to the invention, or a composition according to the invention may be performed by any method known by the person skilled in the art. Use of the methods for delivery of AONs, viral vectors and compositions described herein is included. Contacting may be directly or indirectly and may be in vivo, ex vivo or in vitro.

The invention further provides a method for the treatment of an ABCA4-variant related disease or condition requiring modulating splicing of ABCA4 pre-mRNA of an individual in need thereof, said method comprising contacting a cell, preferably a retina cell, of said individual with an AON according to the invention, or a viral vector according to the invention, or a composition according to the invention, to prevent or block the splicing of exon 39 from said pre-mRNA. The features of this aspect are preferably those defined earlier herein. Contacting the cell, preferably a retina cell with an AON according to the invention, or a viral vector according to the invention, or a composition according to the invention may be performed by any method known by the person skilled in the art. Use of the methods for delivery of AONs, viral vectors and compositions described herein is included. Contacting may be directly or indirectly and may be in vivo, ex vivo or in vitro. Unless otherwise indicated each embodiment as described herein may be combined with another embodiment as described herein.

The sequence information as provided herein should not be so narrowly construed as to require inclusion of erroneously identified bases. The skilled person is capable of identifying such erroneously identified bases and knows how to correct for such errors. All patent and literature references cited in the present specification are hereby incorporated by reference in their entirety.

EXAMPLES

Example 1. Generating and Testing Antisense Oligonucleotides (AONs) for Blocking Exon 39 Skip from Human ABCA4 Pre-mRNA The antisense oligonucleotides tested for their ability the block exon 39 skipping from the human ABCA4 pre-mRNA were designed targeting either exonic or intronic splicing sites (ESS and ISS) present in intron 38 between exon 38 and exon 39, in exon 39, and in intron 39 between exon 39 and exon 40 of the human ABCA4 pre-mRNA, and at the boundaries of the introns and exons (FIGS. 1 and 2A-2B). The aim was to design AONs that were not too long (for manufacturing purposes, for administration efficiency and which would limit self-annealing), that contained at most one CpG motif, and that did not contain a too high percentage of guanosines. All AONs that were initially designed are provided in Table 1. The length of all AONs is in the range of 20 to 25 nucleotides and all AONs are fully 2'-O-methyl modified. All internucleoside linkages are phosphorothioate linkages. After manufacturing the AONs were reconstituted in water to a final concentration of 100 μM.

Construction of Mini-Genes

Human retinoblastoma WERI-Rb-1 (ATCC® HTB-169™) cells were grown in RPMI-1640 Medium (Thermo Scientific; 11875-085), with 10% fetal bovine serum (Biowest; Cat No. S181), and 1% penicillin/streptomycin (Sigma-Aldrich, P4333-100 ML). For DNA isolation one T75 flask of WERI-Rb-1 cells was collected and centrifuged for 5 min at 300×g to collect cell pellet. DNA was extracted using DNeasy Blood & Tissue kits according to manufacturer's instruction. DNA was eluted in 200 μl Buffer AE provided by the kit. To increase the yield, the eluate was passed twice over the same column. DNA concentration was measured using a Nanodrop 2000 spectrophotometer (Nanodrop Technology) and samples were stored at −20° C. for further use.

TABLE 1

Antisense oligonucleotide sequences

| Name | Sequence (5' to 3') | Target region | SEQ ID NO |
|---|---|---|---|
| ABCA4-AON1 | CUCACAGGACAGCACAGGGCAA | Intron38 | 1 |
| ABCA4-AON2 | CAGCAGGUGGGGCCCAGAUGCU | Intron38 | 2 |
| ABCA4-AON3 | CAAACCCCACCCCCCCUCUCUU | Intron38 | 3 |
| ABCA4-AON4 | GUAGGACUGUUGGAAACGGGG | Intron38 | 4 |
| ABCA4-AON5 | AGCGUCUGAAACAGGGAA | Intron38-Exon39 | 5 |
| ABCA4-AON6 | GAACCUGAGCAGCGUCUGAAA | Intron38-Exon39 | 6 |
| ABCA4-AON7 | UGAGCAGCUUCCUCAGCACGG | Exon39 | 7 |
| ABCA4-AON8 | CCCAGGCAGAAGUGGGGGAAG | Exon39 | 8 |
| ABCA4-AON9 | GUGCAAGGUCAAUGAGGCCCC | Exon39 | 9 |
| ABCA4-AON10 | CAAACCGGGCAUAGACAUCU | Exon39 | 10 |
| ABCA4-AON11 | CUCGGCUACCACCCACCAAACC | Exon39-Intron39 | 11 |
| ABCA4-AON12 | CCCAGGGCCCAUGCUCCAUGGGC | Intron39 | 12 |
| ABCA4-AON13 | GUAACCCUCCCAGCUUUGGA | Intron39 | 13 |
| ABCA4-AON14 | GAGCCCCCCGGUAACCCUCCCA | Intron39 | 14 |
| ABCA4-AON15 | AGCACCAGCCCCUGCCACAGUC | Intron39 | 15 |
| ABCA4-AON16 | UGCCACAGUCUGAUGCAGGAGCC | Intron39 | 16 |
| ABCA4-AON17 | CCAGAUGCUCUCACAGGACAGCA | Intron38 | 17 |
| ABCA4-AON18 | GGUGGGGCCCAGAUGCUCUCACA | Intron38 | 18 |
| ABCA4-AON19 | UCUUCAGCAGGUGGGGCCCAGAUG | Intron38 | 19 |
| ABCA4-AON20 | CCCCUCUCUUCAGCAGGUGGGG | Intron38 | 20 |
| ABCA4-AON21 | CCCACCCCCCUCUCUUCAGCA | Intron38 | 21 |
| ABCA4-AON22 | GACUGUUGGAAACGGGCAAACC | Intron38 | 22 |
| ABCA4-AON23 | CAGGGAAGUAGGACUGUUGGAAAC | Intron38 | 23 |
| ABCA4-AON24 | AGCGUCUGAAACAGGGAAGUAGG | Intron38-Exon39 | 24 |
| ABCA4-AON25 | GUUGAACCUGAGCAGCGUCUGAA | Intron38-Exon39 | 25 |
| ABCA4-AON26 | GGGAAGACAAUGAGCAGCUUCCU | Exon39 | 26 |

TABLE 1-continued

Antisense oligonucleotide sequences

| Name | Sequence (5' to 3') | Target region | SEQ ID NO |
|---|---|---|---|
| ABCA4-AON27 | AGGCCCCGGCCCAGGCAGAAGUG | Exon39 | 27 |
| ABCA4-AON28 | GCCUGGCUCAGUGCAAGGUCAAU | Exon39 | 28 |
| ABCA4-AON29 | ACCACCCACCAAACCGGGCAUAGA | Exon39-Intron39 | 29 |
| ABCA4-AON30 | GGGCCUCGGCUACCACCCACCAA | Exon39-Intron39 | 30 |
| ABCA4-AON31 | UGCUCCAUGGGCCUCGGCUACCA | Intron39 | 31 |
| ABCA4-AON32 | GGGCCCAUGCUCCAUGGGCCUCGG | Intron39 | 32 |
| ABCA4-AON33 | CUUUGGACCCGGGCCCAUGCUCCA | Intron39 | 33 |
| ABCA4-AON34 | CCCUCCCAGCUUUGGACCCGGGC | Intron39 | 34 |
| ABCA4-AON35 | GCAGGAGCCCCCCGGUAACCCU | Intron39 | 35 |
| ABCA4-AON36 | CACAGUCUGAUGCAGGAGCCCCC | Intron39 | 36 |
| ABCA4-AON37 | CAGCCCCUGCCACAGUCUGAUGC | Intron39 | 37 |

To generate wild type insert (WT) containing SalI and NotI restriction sites on 5' and 3' ends respectively, 300 ng WERI-Rb-1 DNA was used as template and amplification of the target sequence was done using Phusion® High-Fidelity DNA Polymerase (Thermo Scientific; Cat No. F530L) with the following primer sets:

MG1 WT (Sangermano et al. 2016):
MG1-F
(SEQ ID NO: 51)
5'-AAAAAAGTCGACGTGTTAACAAATGCCTTGAGG-3'

MG1-R
(SEQ ID NO: 52)
5'-AAAAAAGCGGCCGCAGCTCACCCCACAGACCT-3'

MG2 WT (Sangermano et al. 2016):
MG2-F
(SEQ ID NO: 38)
5'-AAAAAAGTCGACCCTTGAGGCACTGCTTGTAA-3'

MG2-R
(SEQ ID NO: 39)
5'-AAAAAAGCGGCCGCCTGCCACAGTCTGATGCAG-3'

MG3 WT (as disclosed herein, exon 39 only):
MG3-F
(SEQ ID NO: 53)
5'-AAAAAAGTCGACAAATCCCTCCAGTGGCCAGT-3'

MG3-R
(SEQ ID NO: 54)
5'-AAAAAAGCGGCCGCCCTAATCCTCTCCAGCTGG-3'

MG4 WT (as disclosed herein, exon 39 and exon 40):
MG4-F
(SEQ ID NO: 53)
5'-AAAAAAGTCGACAAATCCCTCCAGTGGCCAGT-3'

MG4-R
(SEQ ID NO: 55)
5'-AAAAAAGCGGCCGCATATCAGCAATTGAAATT-3'

The MG3 inserts starts at position −150 in intron 38 and ends at +152 in intron 39, whereas the MG4 insert starts at position −150 in intron 38 (same as MG3) and ends at position +246 in intron 40. The resulting PCR product was gel-purified with the NucleoSpin Gel and PCR cleanup kit (Machery-Nagel; Cat No. 740609.250) according to the manufacturer's protocol. The mutant inserts with different lengths of flanking introns were ordered from Integrated DNA Technologies as gBlocks containing SalI and NotI restriction site on 5' and 3' ends respectively.

The DNA inserts (wild type as outlined above and mutant gBlock fragments) and the host vector pET01 Exontrap vector (MoBiTec GmbH; Cat No. K2010) were digested by SalI and NotI and independently ligated together using general procedures known in the art. The presence of the insert in the vector was checked by PCR using the following primer pair: Exon 1 forward: 5'-CCAGGCTTTTGT-CAACAGCA-3' (SEQ ID NO:40) and Exon 2 reverse: 5'-ATTGCAGAGGGGTGGACAG-3' (SEQ ID NO:41). The resulting constructs bearing part of intron 38 (with and without mutation) and whole exon 39, and part of intron 39 (MG1, MG2 and MG3) are shown schematically in FIG. 4 (upper panel).

Figure 4:
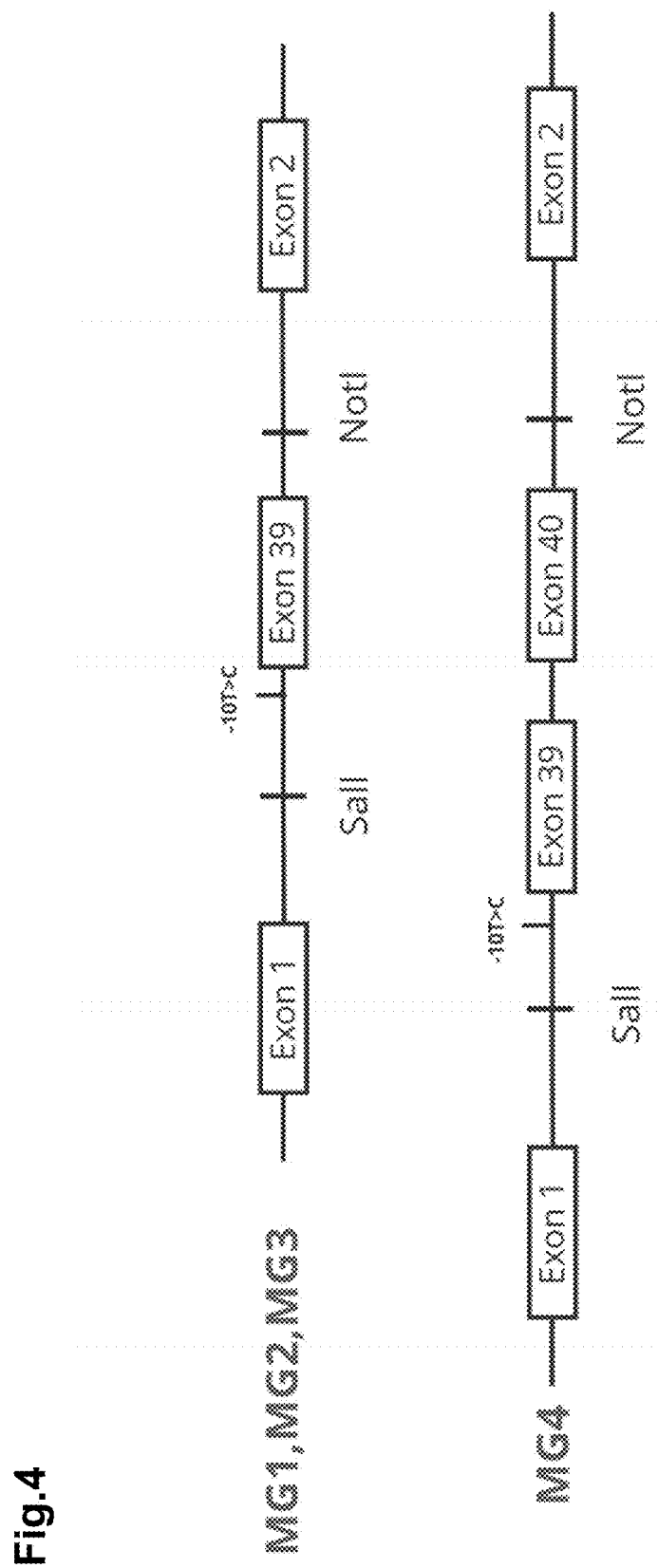
FIG. 4 is a schematic representation of the mini gene (MG) constructs, showing the SalI and NotI cloning sites and the position of the c.5461-10T>C mutation (−10T>C) in intron 38. MG1 and MG2 have been described in Sangermano et al. (2016). MG3 (with exon 39) and MG4 (with exon 39 and exon 40) are as disclosed herein.
Figure 5:
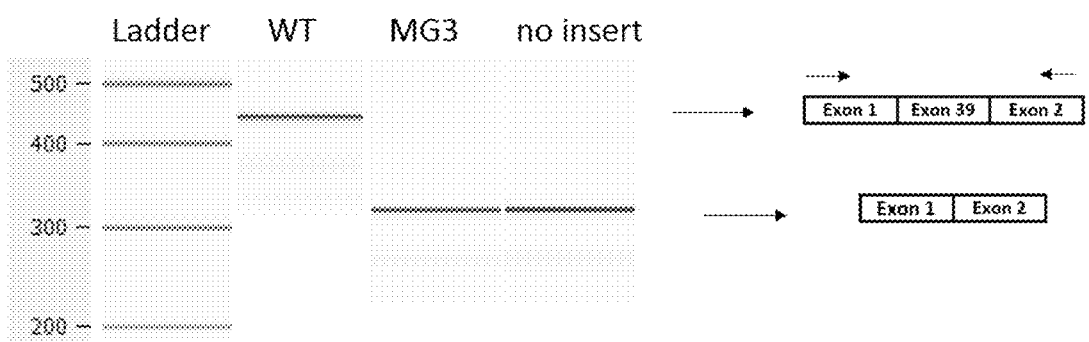
FIG. 5 shows that the MG3 construct (when carrying the c.5461-10T>C mutation) is 'functional' in the sense that after transfection into HeLa cells, the transcribed pre-mRNA is processed such that exon 39 is spliced out and exon 1 is linked to exon 2, whereas in the absence of the mutation (lane WT, with the wild type mini gene construct) exon 39 remains present between exon 1 and exon 2. The no insert lane is a control showing the PCR product when no insert is included in the mini gene construct.

A similar approach was used to obtain a construct that includes part of intron 38 (with and without mutation), the whole of exon 39, the whole of intron 39, the whole of exon 40, and part of intron 40 in a single vector to investigate the block of exon 39/exon 40 double skipping by using the AONs of the present invention. The construct containing exon 39 and exon 40 together with the mutation location in intron 38 upstream of exon 39 (MG4) is shown in FIG. 4 (lower panel).

Cell Culture, Transfections, RNA Isolation and cDNA Synthesis

HeLa cells were cultured in DMEM supplemented with 10% FBS and 1% pen/strep. Cells were seeded with $2 \times 10^5$ cells/wells onto 24 well plates. For sequential transfections, one day after seeding the cells were transfected with 200-500 ng plasmid using Lipofectamin 2000 (Thermo Scientific, 11668019) in 1 ml DMEM supplemented with 10% FBS and incubated for 6 h, after which the medium was refreshed. After 24 h, cells were transfected with 100-250 nM AON in 500 μl medium. RNA was isolated 24 h post AON transfection. For double transfection, one day after seeding the cells were co-transfected with 200-500 ng plasmid+250 nM AON in 500 μL DMEM with 10% FBS using Lipofectamin 3000 (Thermo Scientific, L3000015).

After 6 h incubation, medium was refreshed. RNA was isolated after 24-48 h. For this, cells were washed with PBS and lysed with 350 µl RLT buffer (Qiagen, RNeasy Plus Mini kit, #74136). RNA was isolated using the RNeasy Plus Mini kit (Qiagen, #74136) according to the manufacturer's instruction. Genomic DNA was removed using gDNA Eliminator columns supplied with the kit. RNA was eluted in 30 µl RNAse-free water. To increase the yield, the eluate was passed twice over the same column. RNA concentrations were measured using a Nanodrop 2000 spectrophotometer (Nanodrop Technology) and samples were stored at −80° C. for further use. For cDNA synthesis, 1000 ng RNA was used as template for Maxima Reverse Transcriptase (Thermo Scientific; Cat No. EP0742) with random hexamer primers and processed according to the manufacturer's instruction. A non-RT sample (without enzyme) was included as control and analyzed along with the other samples.

PCR, Bioanalyzer and ddPCR

In principal, a fragment of the ABCA4 mRNA—when it still contains exon 39—can specifically be amplified by using PCR when one or both PCR primers are within that exon. To see whether the exon 39 was still present in the mRNA, 100 ng cDNA was generated and used as template and amplification of the target sequence. This was done using the following primers: Exon 39 forward: 5'-CTGCT-CATTGTCTTCCCCCA-3' (SEQ ID NO:42) and Exon 39 reverse: 5'-CAAACCGGGCATAGACATCTG-3' (SEQ ID NO:43). Both these primers anneal in the exon 39 sequence, which makes that background mRNA containing exon 39 (in the HeLa cells) will be co-amplified. The PCR reaction was carried out using Phusion® High-Fidelity DNA Polymerase (Thermo Scientific; Cat No. F530L). PCR fragments were analyzed with the Bioanalyzer 2100 (DNA 1000 kit, Agilent Technologies), using the Bioanalyzer 2100 software.

For ddPCR analysis, samples are analyzed using the QX200™ Droplet Digital™ PCR System (Bio-Rad). A custom made assay is generated (IDT, Integrated DNA Technologies), consisting of primers amplifying exon 1 and 2 of the plasmid and 2 probes to target ABCA4 exon 39 and plasmid exon 1. Experimental set-up and analysis are performed according to manufacturer's protocol (Bio-Rad, QX200 system).

Results

FIG. 6 shows the RT-PCR results on a Bioanalyzer after transfection of HeLa cells with MG3 construct carrying the c.5461-10T>C mutation (+MG3 mut.) or MG3 wild type construct (+MG3 WT), with and without different AONs. Initially the sixteen AONs of SEQ ID NO:1 to 16 were tested (see FIGS. 2A-2B and Table 1). The RT-PCR was performed with primers annealing within the exon 39 sequence, which makes that the lane indicated with "HeLa(NT)" (non-transfected HeLa cells) in the lower panel also shows a band at the expected level. This is due to the fact that HeLa cells carry the wild type ABCA4 gene, from which apparently mRNA is produced and from which also then a positive PCR product is generated. The negative control ("ctrAON") was a transfection with MG3 construct with the mutation and an unrelated non-ABCA4 annealing AON. Another negative control is the "Mock tr" lane that represents cells that were transfected only with the transfection reagents, not with constructs or AON. "Rt-ctr" and "H₂O" were two additional negative controls for the PCR reaction, without cell material, displaying no signal.

An increase in intensity of the product band suggests an increase of mRNA copies comprising exon 39. Because such should be assessed based on what is already generated in HeLa cells as a background, and in fact relative to the WT signal wherein no AON is transfected, the lane indicated with "WT-no AON" was taken as 100% and the Bioanalyzer software was applied to measure the intensity of the other bands in comparison to that 100% intensity. This shows that approximately ⅓ (29%) is at least due to the background HeLa alone signal, although—because it is a PCR reaction—is not the ultimate best measure to indicate differences in expression levels. The data show that transfection itself with or without AON is able to give an AON-unrelated boost of the signal to around 70% using this setup. However, the intensity detected with AON1, AON3, AON4, AON5, AON6, AON12, AON13, and AON14 was increased to at least 80%, with AON3, AON4, AON6, and AON12 performing best, with intensities of at least 90% of the WT signal, set at 100%. This shows that these AONs were able to inhibit exon 39 skipping from the MG3 construct, which carries the c.5461-10T>C mutation, to levels that are close to the wild type situation in which exon 39 is not skipped.

Example 2. Additional Testing of AONs for Blocking Exon 39 Skip from Human ABCA4 Pre-mRNA in HEK293 Cells Using ddPCR Analysis The antisense oligonucleotides that were described and initially tested in Example 1 were further assessed in HEK293 cells using quantitative and isoform-specific ddPCR assays. In brief, an ABCA4 exon 39 mini-gene containing the c.5461-10T>C mutation (MG3) was transiently expressed in HEK293 cells and treated with different AONs. Non-AON treated (mock) sample was used as a reference control. ddPCR assays were used to quantify the ability of AONs to block the skipping of exon 39 from human ABCA4 pre-mRNA.

Cell Culture Conditions, Transfections, RNA Isolation

MG3 was described in Example 1. HEK293 cells were cultured in DMEM supplemented with 10% FBS and 1% pen/strep. Cells were seeded at a density of $0.2 \times 10^6$ cells/well onto 12 well plates. Two samples (replicates) were used per treatment condition. For double transfections, one day after seeding, the cells were transfected with 75 ng MG3 plasmid and 250 nM AON using LipofectAMINE™ 2000 (Invitrogen), 1:2 ratio w/v, in 1 mL DMEM supplemented with 10% FBS. RNA was isolated 24 hrs post transfection using the RNeasy Plus Mini kit (Qiagen, #74136) according to the manufacturer's instructions. RNA concentrations were measured using a Nanodrop 2000 spectrophotometer (Nanodrop Technology) and samples were stored at −80° C. for further use.

ddPCR Quantification ddPCR was performed using the One-Step RT-ddPCR Advanced Kit for Probes (Bio-Rad) according to the supplier's protocol on the QX200 system (Bio-Rad). Assays contained 900 nM forward and reverse primer each and 250 nM labelled probe. For AON 7, 8, 9, 10, 11, 26, 27, 28, and 29 exon 39 inclusion was assessed using 5'-AGCTCTC-TACCTGGTGTGT-3' (SEQ ID NO:56) as forward primer and 5'-AACCTGAGCAGCGTCTTG-3' (SEQ ID NO:57) as reverse primer and 5'-TTCTTCTACACACC-CATGTCCCGC-3' (SEQ ID NO:58) as probe. For the remainder of the AONs, exon 39 inclusion was assessed using 5'-GTCAACAGCACCTTTGTGGT-3' (SEQ ID NO:59) as forward primer, 5'-TGTGCCACC-CAAACCGGG-3' (SEQ ID NO:60) as reverse primer and 5'-GGTCAATGAGGCCCCGGCCCAGGCA-3' (SEQ ID NO:61) as probe. Exon 39 exclusion was assessed using 5'-GTCAACAGCACCTTTGTGGT-3' (SEQ ID NO:62) as forward primer, 5'-CAAGGTCTGAAGGTCACGGG-3' (SEQ ID NO:63) as reverse primer and 5'-AGGACC-CACAAGGTGGCACAA-3' (SEQ ID NO:64) as probe. The percentage exon 39 inclusion was calculated using the formula: (exon 39 inclusion*100)/(exon 39 inclusion+exon 39 exclusion).

Figure 7A:
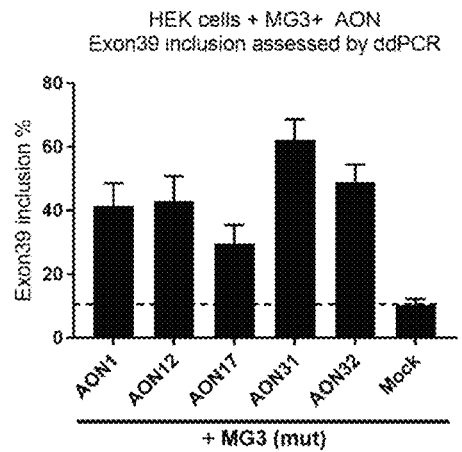
FIGS. 7A-7C show the ddPCR quantification of percentage of exon 39 inclusion in HEK293 cells transfected with MG3 construct and a variety of AONs as indicated. The three panels A, B and C represent experiments performed on three different days, but performed in an identical manner. Mock represents the percentage exon 39 inclusion when no AON is transfected.
Figure 7B:
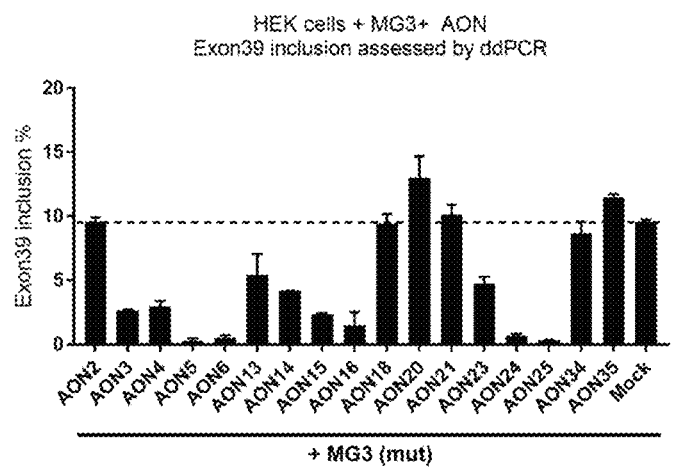
Figure 7C:
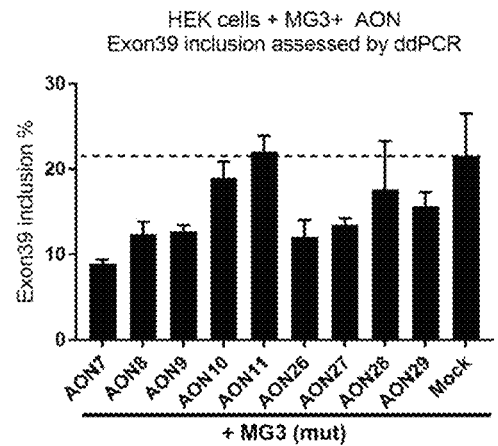

Results ddPCR quantification of percentage of exon 39 inclusion in HEK293 cells transfected with MG3 construct carrying the c.5461-10T>C mutation and AON(s) is shown in FIGS. 7A-7C. AONs were assessed in batches on different days so the results are depicted per experiment with matched non-AON treated (mock) control. Data is shown as mean±standard deviation. In untreated "mock" condition exon 39 inclusion was observed in approximately 10% of the transcripts. Many AONs were able to increase the percentage of transcripts with exon 39 inclusion, compared to mock. As can be observed in FIG. 7A, AON31 showed the highest percentage of inclusion (i.e. 62%) followed by AON32, AON12 and AON1 which showed percentages of 49%, 43% and 41% respectively. AON17, AON20 and AON35 also resulted in an increase of exon inclusion albeit to a lower extent.

Importantly, AON12, AON31 and AON32 bind to an overlapping region in intron 39 of the ABCA4 pre-mRNA, indicating the presence of a hotspot with the following sequence: 5'-UGGUAGCCGAGGCCCAUGGAG-CAUGGGCCCUGGG-3' (SEQ ID NO:65). Also AON1 and AON17 bind to overlapping regions, indicating the presence of a hotspot in intron 38 (5'-UUGCCCUGUGCUGUCCU-GUGAGAGCAUCUGG-3' (SEQ ID NO:66). Both hotspots are indicated in italic font in FIGS. 2A-2B.

Example 3. Testing AONs for Blocking Exon 39 Skip from Human ABCA4 pre-mRNA Using an Alternative (MG3_2) Mini-Gene Construct A variety of AONs that were described and tested as shown in Example 1 and Example 2 were further assessed using a new mini-gene construct. In brief, a new ABCA4 exon 39 mini-gene containing the c.5461-10T>C mutation (herein referred to as MG3_2) was transiently expressed in HEK293 cells and treated with different AONs. Non-AON treated (mock) samples were used as reference controls. Additionally, a scrambled AON that is not complementary to ABCA4 pre-mRNA was used as a control. Quantitative and isoform specific ddPCR assays were used to quantify the ability of AONs to block the skipping of exon 39 from human ABCA4 pre-mRNA.

Construction of Mini-Gene MG3_2

A DNA insert comprising the ABCA4 exon 39 sequence and its flanking intronic regions, including the c.5461-10T>C mutation was chemically synthesized as a gBlock carrying EcoR1 and SalI sites (Integrated DNA Technologies) at the 5' and 3' ends respectively and inserted in the pCI-neo-mammalian splice vector (described in WO 2016/005514; WO 2017/186739) leaving all sequences (except the human ABCA4 intron38-exon39-intron39 sequences) intact. FIG. 8 shows the sequence of the MG3_2 construct and the positions therein of the ABCA4 sequences.

Cell Culture, Transfections, RNA Isolation

HEK293 cells were cultured and seeded as described in Example 2. For sequential transfections, one day after seeding, the cells were transfected with 50 ng plasmid using maxPEI (Polysciences) with a DNA:PEI ratio of 1:3 w/w in 1 mL DMEM supplemented with 10% FBS. After 24 hrs, cells were transfected with 250 nM AON using LipofectAMINE™ 2000 (Invitrogen), 1:2 w/v ratio, in 1 mL medium. RNA was isolated 24 hrs post AON transfection using RNeasy Plus Mini kit (Qiagen) according to the manufacturer's instructions. RNA concentrations were measured using a Nanodrop 2000 spectrophotometer (Nanodrop Technology) and samples were stored at −80° C. for further use.

ddPCR Quantification ddPCR was performed as described in Example 2. Exon 39 inclusion was assessed using 5'-TACATGTTCGTGGTC-CACTTC-3' (SEQ ID NO:70) as forward primer, 5'-GAA-GACAATGAGCAGCTTCCT-3' (SEQ ID NO:71) as reverse primer and 5'-AACGCTGCTCAGGTTCAACGC-3' (SEQ ID NO:72) as probe. Exon 39 exclusion was assessed using the primer of SEQ ID NO:70 as forward primer, 5'-GCAGATGGTGGTGAGCAT-3' (SEQ ID NO:73) as reverse primer and 5'-ACCGTCAAGGAGTTCCG-GAACTG-3' (SEQ ID NO:74) as probe. Percentage of exon 39 inclusion was calculated as in Example 2.

Results

Figure 9A:
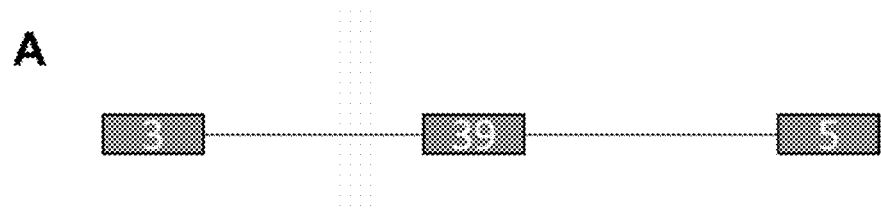
FIGS. 9A-9C show in (A) the schematic outline of the MG3_2 mini-gene construct. It also shows in (B) the position of the amplified product from MG3_2 (plasmid alone) in HEK293 cells with exon 39 included and excluded on a bioanalyzer. Due to the c.5461-10T>C mutation, most of the transcripts lacked exon 39 (lower band) and exon 39 inclusion (upper band) was observed at much lower levels. ddPCR quantification of percentage of exon 39 inclusion in HEK293 cells transfected with MG3_2 construct carrying the c.5461-10T>C mutation and the different AON(s) is shown in (C), revealing the strong exon 39 inclusion effects of subsequent transfection with AON1, 3, 4, 9, 12, 17, 24, 25, 29, 31, or 32.
Figure 9B:
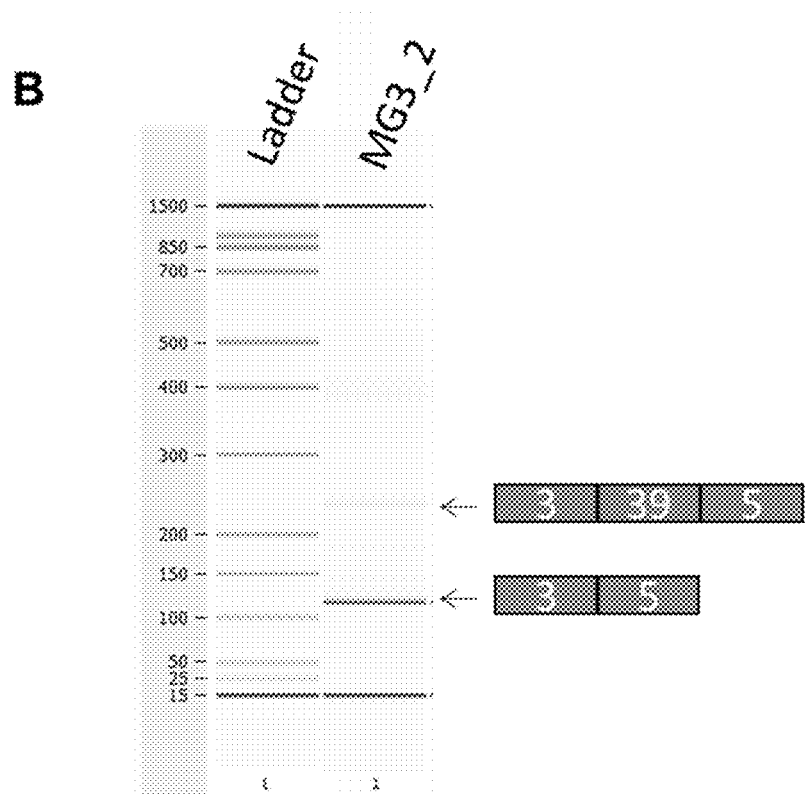
Figure 9C:
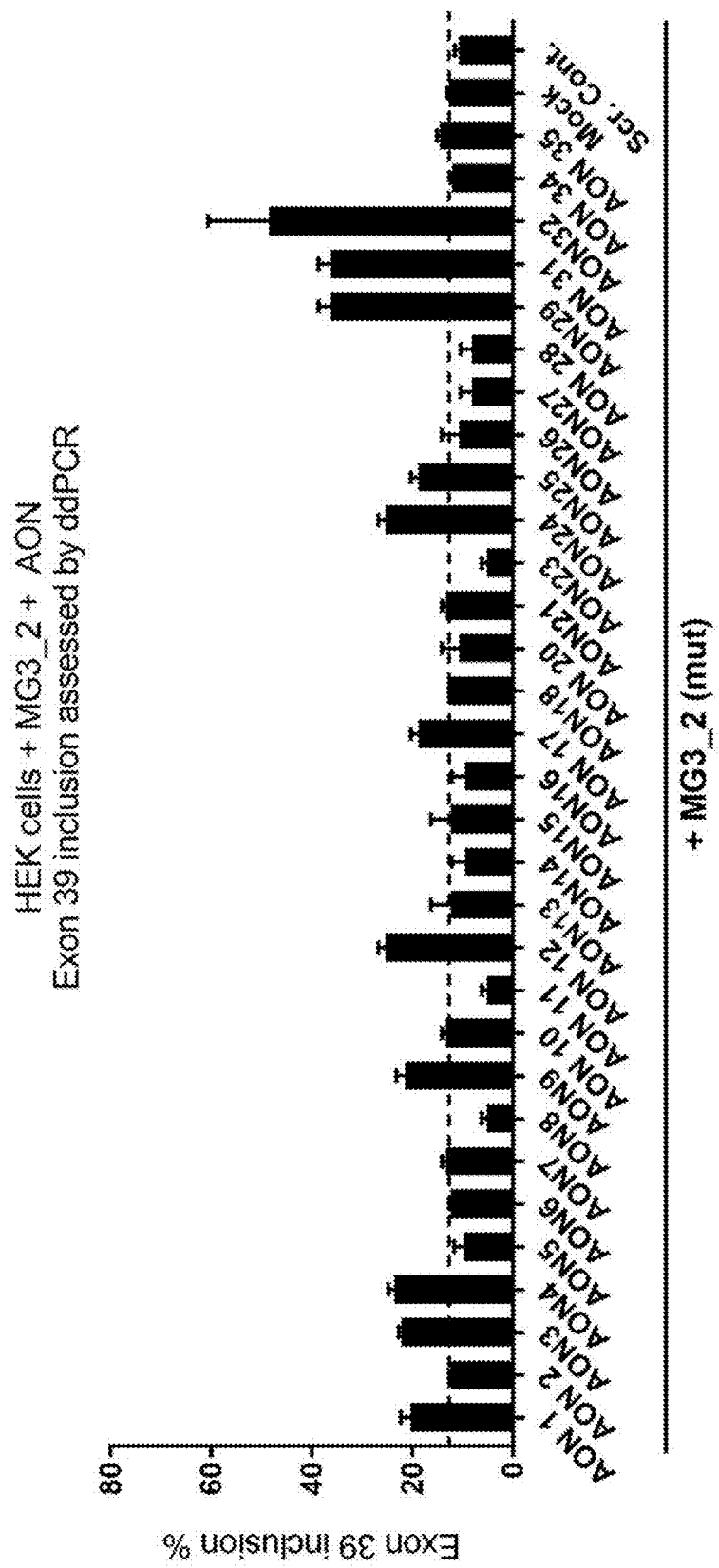

FIG. 9A shows a schematic version of the MG3_2 mini-gene construct. Initially, HEK293 cells were transfected with plasmid alone and the RNA was PCR amplified using primers from the RHO exon 3 and 5 areas. PCR product was analysed on a bioanalyzer (FIG. 9B). Due to the c.5461-10T>C mutation, most of the transcripts lacked exon 39 (lower band) and in fact exon 39 inclusion (upper band) was observed at much lower levels.

ddPCR quantification of percentage of exon 39 inclusion in HEK293 cells transfected with MG3_2 construct carrying the c.5461-10T>C mutation and AON(s) is shown in FIG. 9C. Data is shown as mean±standard deviation. Scrambled control (given as Scr. Cont) refers to transfection with MG3_2 construct and an unrelated non-complementary AON. "Mock" refers to no AON treatment (negative control). In mock conditions exon 39 inclusion was observed in 11% of the transcripts. Many AONs were able to increase this background percentage. AON32 gave the highest percentage of exon 39 inclusion (49%), which is in line with the results discussed in Example 2. Once again, AON32 overlaps with AON31 and AON12 which also increased the amount of exon 39 inclusion. This confirms that the sequence of SEQ ID NO:65 indeed represents a hotspot for AON annealing and induction of exon 39 retention. AON1 and AON17 which resulted in an increase of exon 39 inclusion in Example 2 also showed positive effect in this study, which confirms that also the sequence of SEQ ID NO:66 represents a hotspot for AON annealing and induction of exon 39 retention. Other AONs that showed an increase in exon 39 inclusion were AON3, 4, 9, 24, 25, and 29.

Figure 10:
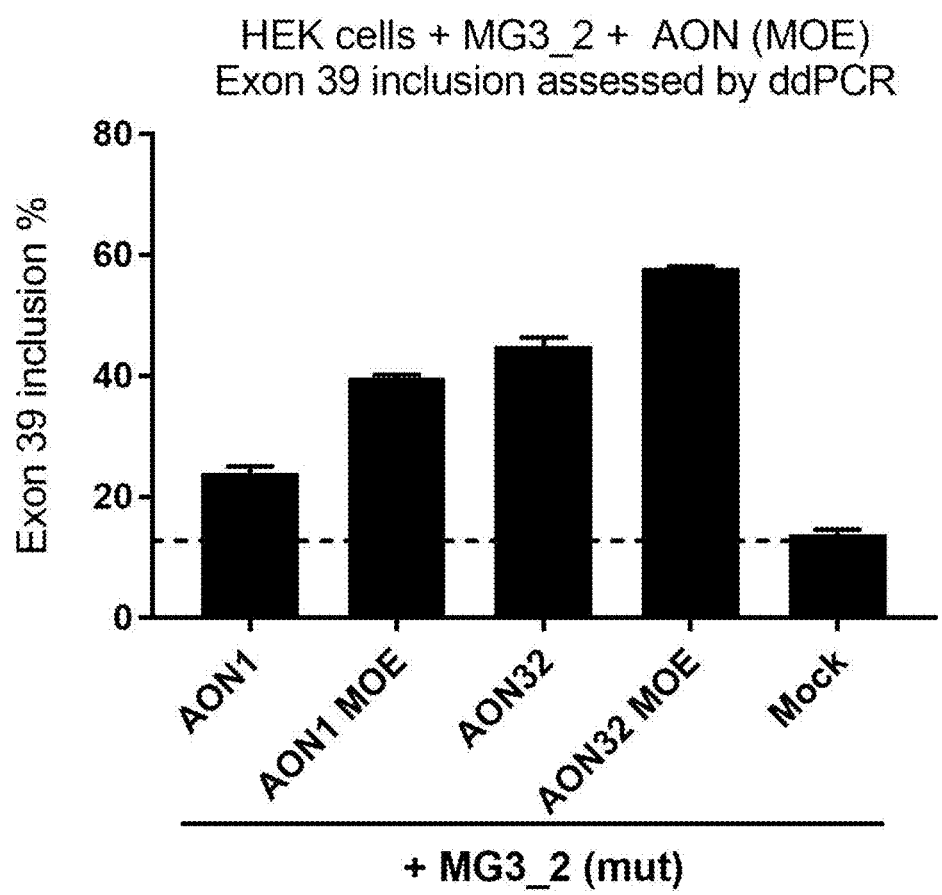
FIG. 10 shows the percentage of exon 39 inclusion, using ddPCR, after transfection with the MG3_2 mini gene and AON1 and AON32 that are fully modified with 2'-OMe modifications in the sugar moieties, in HEK293 cells, in comparison to AON1 and AON32 that instead of a 2'-OMe modification carry 2'-MOE modifications in each sugar moiety, and a mock transfection where no AON was used. A significant increase in effect is observed when 2'-MOE versions of the same oligonucleotides are being applied.

Example 4. AONs with 2'-O-methoxyethyl (2'-MOE) Modification for Blocking Exon 39 Skip from Human ABCA4 pre-mRNA To further address the effects of AONs on exon 39 inclusion, AON1 and AON32 were generated with a 2'-O-methoxyethyl (2'-MOE) modification in each nucleoside and compared to AON1 and AON32 that comprised a 2'-OMe modification in each nucleoside (as they were used in the examples above). The ability of AON1-MOE and AON32-MOE to block the skipping of exon 39 from human ABCA4 pre-mRNA was assessed and compared to AON1 and AON32. In brief, ABCA4 exon 39 mini-gene containing the c.5461-10T>C mutation (MG3_2, see Example 3) was transiently expressed in HEK293 cells and treated with the different AONs. Non-AON treated sample was used as a reference control. Quantitative and isoform specific ddPCR assays were used to quantify the ability of AONs to block the skipping of exon 39 from human ABCA4 pre-mRNA. HEK293 cells were cultured, seeded as described above and 250 nM AON was transfected in the context of 50 ng plasmid. ddPCR was performed and exon inclusion percentage calculations were as described in Example 3. Results are shown in FIG. 10, as mean±standard deviation. "Mock" refers to no AON treatment (i.e. negative control). In untreated "mock" condition exon 39 inclusion was observed in approximately 14% of the transcripts, which was significantly increased after treatment with AON1 and AON32 (both with 2'-OMe modifications) in line with what was observed in Example 3. The AON1 effect (approximately 24% of transcripts retained exon 39) was increased to approximately 40% with AON1 MOE, indicating the improved and more efficient exon 39 retention when using a (most likely more stable) 2'-MOE modified oligonucleotide. A similar trend was noticed for AON32. In the AON32 (2'-O-methyl chemistry) treated sample, approximately 45% of transcripts retained exon 39, whereas in the AON32 MOE (2'-O-methoxyethyl chemistry) treated sample, approximately 58% of transcripts retained exon 39.

---

The invention claimed is:

1. An antisense oligonucleotide (AON) that is able to inhibit skipping of at least one exon in human ABCA4 pre-mRNA, wherein the exon skipping is due to a c.5461-10T>C mutation in intron 38 of the human ABCA4 gene, wherein said AON comprises or consists of the sequence of any of SEQ ID NO: 12, 31 and 32, wherein said AON has at least one phosphorothioate linkage.

2. The AON according to claim 1, wherein said AON is an oligoribonucleotide (RNA oligonucleotide) comprising at least one 2'-O alkyl modification.

3. The AON according to claim 1, wherein said AON is an oligoribonucleotide (RNA oligonucleotide) comprising at least one 2'-methoxyethoxy (2'-MOE) modification.

4. A pharmaceutical composition comprising the AON according to claim 1, and a pharmaceutically acceptable carrier, wherein the pharmaceutical composition is for intravitreal administration.

5. A viral vector expressing antisense oligonucleotide (AON) that is able to inhibit skipping of at least one exon in human ABCA4 pre-mRNA, wherein the exon skipping is due to a c.5461-10T>C mutation in intron 38 of the human ABCA4 gene, wherein said AON comprises or consists of the sequence of any of SEQ ID NO: 12, 31 and 32.

* * * * *

SEQUENCE LISTING

```
<160> NUMBER OF SEQ ID NOS: 74

<210> SEQ ID NO 1
<211> LENGTH: 22
<212> TYPE: RNA
<213> ORGANISM: Artificial Sequence
<220> FEATURE:
<223> OTHER INFORMATION: AON1

<400> SEQUENCE: 1
cucacaggac agcacagggc aa                                              22

<210> SEQ ID NO 2
<211> LENGTH: 22
<212> TYPE: RNA
<213> ORGANISM: Artificial Sequence
<220> FEATURE:
<223> OTHER INFORMATION: AON2

<400> SEQUENCE: 2
cagcaggugg ggcccagaug cu                                              22

<210> SEQ ID NO 3
<211> LENGTH: 22
<212> TYPE: RNA
<213> ORGANISM: Artificial Sequence
<220> FEATURE:
<223> OTHER INFORMATION: AON3

<400> SEQUENCE: 3 caaacoccac cccccucuc uu                                               22

<210> SEQ ID NO 4
<211> LENGTH: 21
<212> TYPE: RNA
<213> ORGANISM: Artificial Sequence
<220> FEATURE:
<223> OTHER INFORMATION: AON4

<400> SEQUENCE: 4
guaggacugu uggaaacggg g                                               21

<210> SEQ ID NO 5
<211> LENGTH: 18
<212> TYPE: RNA
<213> ORGANISM: Artificial Sequence
<220> FEATURE:
<223> OTHER INFORMATION: AON5

<400> SEQUENCE: 5
agcgucugaa acagggaa                                                   18
```

```
<210> SEQ ID NO 6
<211> LENGTH: 21
<212> TYPE: RNA
<213> ORGANISM: Artificial Sequence
<220> FEATURE:
<223> OTHER INFORMATION: AON6

<400> SEQUENCE: 6
gaaccugagc agcgucugaa a                                              21

<210> SEQ ID NO 7
<211> LENGTH: 21
<212> TYPE: RNA
<213> ORGANISM: Artificial Sequence
<220> FEATURE:
<223> OTHER INFORMATION: AON7

<400> SEQUENCE: 7
ugagcagcuu ccucagcacg g                                              21

<210> SEQ ID NO 8
<211> LENGTH: 21
<212> TYPE: RNA
<213> ORGANISM: Artificial Sequence
<220> FEATURE:
<223> OTHER INFORMATION: AON8

<400> SEQUENCE: 8
cccaggcaga aguggggaa g                                               21

<210> SEQ ID NO 9
<211> LENGTH: 21
<212> TYPE: RNA
<213> ORGANISM: Artificial Sequence
<220> FEATURE:
<223> OTHER INFORMATION: AON9

<400> SEQUENCE: 9
gugcaagguc aaugaggccc c                                              21

<210> SEQ ID NO 10
<211> LENGTH: 20
<212> TYPE: RNA
<213> ORGANISM: Artificial Sequence
<220> FEATURE:
<223> OTHER INFORMATION: AON10

<400> SEQUENCE: 10
caaaccgggc auagacaucu                                                20

<210> SEQ ID NO 11
<211> LENGTH: 22
<212> TYPE: RNA
<213> ORGANISM: Artificial Sequence
<220> FEATURE:
<223> OTHER INFORMATION: AON11

<400> SEQUENCE: 11
cucggcuacc acccaccaaa cc                                             22

<210> SEQ ID NO 12
<211> LENGTH: 23
<212> TYPE: RNA
<213> ORGANISM: Artificial Sequence
<220> FEATURE:
<223> OTHER INFORMATION: AON12
```

```
<400> SEQUENCE: 12
cccagggccc augcuccaug ggc                                            23

<210> SEQ ID NO 13
<211> LENGTH: 20
<212> TYPE: RNA
<213> ORGANISM: Artificial Sequence
<220> FEATURE:
<223> OTHER INFORMATION: AON13

<400> SEQUENCE: 13
guaacccucc cagcuuugga                                                20

<210> SEQ ID NO 14
<211> LENGTH: 23
<212> TYPE: RNA
<213> ORGANISM: Artificial Sequence
<220> FEATURE:
<223> OTHER INFORMATION: AON14

<400> SEQUENCE: 14
gagccccccc gguaacccuc cca                                            23

<210> SEQ ID NO 15
<211> LENGTH: 22
<212> TYPE: RNA
<213> ORGANISM: Artificial Sequence
<220> FEATURE:
<223> OTHER INFORMATION: AON15

<400> SEQUENCE: 15
agcaccagcc ccugccacag uc                                             22

<210> SEQ ID NO 16
<211> LENGTH: 23
<212> TYPE: RNA
<213> ORGANISM: Artificial Sequence
<220> FEATURE:
<223> OTHER INFORMATION: AON16

<400> SEQUENCE: 16
ugccacaguc ugaugcagga gcc                                            23

<210> SEQ ID NO 17
<211> LENGTH: 23
<212> TYPE: RNA
<213> ORGANISM: Artificial Sequence
<220> FEATURE:
<223> OTHER INFORMATION: AON17

<400> SEQUENCE: 17
ccagaugcuc ucacaggaca gca                                            23

<210> SEQ ID NO 18
<211> LENGTH: 23
<212> TYPE: RNA
<213> ORGANISM: Artificial Sequence
<220> FEATURE:
<223> OTHER INFORMATION: AON18

<400> SEQUENCE: 18
ggugggnccc agaugcucuc aca                                            23

<210> SEQ ID NO 19
```

```
<211> LENGTH: 24
<212> TYPE: RNA
<213> ORGANISM: Artificial Sequence
<220> FEATURE:
<223> OTHER INFORMATION: AON19

<400> SEQUENCE: 19
ucuucagcag gugggccca gaug                                              24

<210> SEQ ID NO 20
<211> LENGTH: 22
<212> TYPE: RNA
<213> ORGANISM: Artificial Sequence
<220> FEATURE:
<223> OTHER INFORMATION: AON20

<400> SEQUENCE: 20 cccucucuu cagcaggugg gg                                                22

<210> SEQ ID NO 21
<211> LENGTH: 22
<212> TYPE: RNA
<213> ORGANISM: Artificial Sequence
<220> FEATURE:
<223> OTHER INFORMATION: AON21

<400> SEQUENCE: 21
cccacccccc cucucuucag ca                                               22

<210> SEQ ID NO 22
<211> LENGTH: 23
<212> TYPE: RNA
<213> ORGANISM: Artificial Sequence
<220> FEATURE:
<223> OTHER INFORMATION: AON22

<400> SEQUENCE: 22
gacuguugga acggggcaa acc                                               23

<210> SEQ ID NO 23
<211> LENGTH: 24
<212> TYPE: RNA
<213> ORGANISM: Artificial Sequence
<220> FEATURE:
<223> OTHER INFORMATION: AON23

<400> SEQUENCE: 23
cagggaagua ggacuguugg aaac                                             24

<210> SEQ ID NO 24
<211> LENGTH: 23
<212> TYPE: RNA
<213> ORGANISM: Artificial Sequence
<220> FEATURE:
<223> OTHER INFORMATION: AON24

<400> SEQUENCE: 24
agcgucugaa acagggaagu agg                                              23

<210> SEQ ID NO 25
<211> LENGTH: 23
<212> TYPE: RNA
<213> ORGANISM: Artificial Sequence
<220> FEATURE:
<223> OTHER INFORMATION: AON25

<400> SEQUENCE: 25
```

```
guugaaccug agcagcgucu gaa                                              23

<210> SEQ ID NO 26
<211> LENGTH: 23
<212> TYPE: RNA
<213> ORGANISM: Artificial Sequence
<220> FEATURE:
<223> OTHER INFORMATION: AON26

<400> SEQUENCE: 26
gggaagacaa ugagcagcuu ccu                                              23

<210> SEQ ID NO 27
<211> LENGTH: 23
<212> TYPE: RNA
<213> ORGANISM: Artificial Sequence
<220> FEATURE:
<223> OTHER INFORMATION: AON27

<400> SEQUENCE: 27
aggccccggc ccaggcagaa gug                                              23

<210> SEQ ID NO 28
<211> LENGTH: 23
<212> TYPE: RNA
<213> ORGANISM: Artificial Sequence
<220> FEATURE:
<223> OTHER INFORMATION: AON28

<400> SEQUENCE: 28
gccuggcuca gugcaagguc aau                                              23

<210> SEQ ID NO 29
<211> LENGTH: 24
<212> TYPE: RNA
<213> ORGANISM: Artificial Sequence
<220> FEATURE:
<223> OTHER INFORMATION: AON29

<400> SEQUENCE: 29
accacccacc aaaccgggca uaga                                             24

<210> SEQ ID NO 30
<211> LENGTH: 23
<212> TYPE: RNA
<213> ORGANISM: Artificial Sequence
<220> FEATURE:
<223> OTHER INFORMATION: AON30

<400> SEQUENCE: 30
gggccucggc uaccacccac caa                                              23

<210> SEQ ID NO 31
<211> LENGTH: 23
<212> TYPE: RNA
<213> ORGANISM: Artificial Sequence
<220> FEATURE:
<223> OTHER INFORMATION: AON31

<400> SEQUENCE: 31
ugcuccaugg gccucggcua cca                                              23

<210> SEQ ID NO 32
<211> LENGTH: 24
<212> TYPE: RNA
```

```
<213> ORGANISM: Artificial Sequence
<220> FEATURE:
<223> OTHER INFORMATION: AON32

<400> SEQUENCE: 32
gggcccaugc uccaugggcc ucgg                                              24

<210> SEQ ID NO 33
<211> LENGTH: 24
<212> TYPE: RNA
<213> ORGANISM: Artificial Sequence
<220> FEATURE:
<223> OTHER INFORMATION: AON33

<400> SEQUENCE: 33
cuuuggaccc gggcccaugc ucca                                              24

<210> SEQ ID NO 34
<211> LENGTH: 23
<212> TYPE: RNA
<213> ORGANISM: Artificial Sequence
<220> FEATURE:
<223> OTHER INFORMATION: AON34

<400> SEQUENCE: 34
cccucccagc uuuggacccg␣ggc                                               23

<210> SEQ ID NO 35
<211> LENGTH: 23
<212> TYPE: RNA
<213> ORGANISM: Artificial Sequence
<220> FEATURE:
<223> OTHER INFORMATION: AON35

<400> SEQUENCE: 35
gcaggagccc ccccgguaac ccu                                               23

<210> SEQ ID NO 36
<211> LENGTH: 23
<212> TYPE: RNA
<213> ORGANISM: Artificial Sequence
<220> FEATURE:
<223> OTHER INFORMATION: AON36

<400> SEQUENCE: 36
cacagucuga ugcaggagcc ccc                                               23

<210> SEQ ID NO 37
<211> LENGTH: 23
<212> TYPE: RNA
<213> ORGANISM: Artificial Sequence
<220> FEATURE:
<223> OTHER INFORMATION: AON37

<400> SEQUENCE: 37
cagccccugc cacagucuga ugc                                               23

<210> SEQ ID NO 38
<211> LENGTH: 32
<212> TYPE: DNA
<213> ORGANISM: Artificial Sequence
<220> FEATURE:
<223> OTHER INFORMATION: MG2-F primer

<400> SEQUENCE: 38
aaaaaagtcg acccttgagg cactgcttgt aa                                     32
```

<210> SEQ ID NO 39
<211> LENGTH: 33
<212> TYPE: DNA
<213> ORGANISM: Artificial Sequence
<220> FEATURE:
<223> OTHER INFORMATION: MG2-R primer

<400> SEQUENCE: 39
aaaaaagcgg ccgcctgcca cagtctgatg cag                          33

<210> SEQ ID NO 40
<211> LENGTH: 20
<212> TYPE: DNA
<213> ORGANISM: Artificial Sequence
<220> FEATURE:
<223> OTHER INFORMATION: Exon 1 forward primer

<400> SEQUENCE: 40
ccaggctttt gtcaacagca                                         20

<210> SEQ ID NO 41
<211> LENGTH: 19
<212> TYPE: DNA
<213> ORGANISM: Artificial Sequence
<220> FEATURE:
<223> OTHER INFORMATION: Exon 2 reverse primer

<400> SEQUENCE: 41
attgcagagg ggtggacag                                          19

<210> SEQ ID NO 42
<211> LENGTH: 20
<212> TYPE: DNA
<213> ORGANISM: Artificial Sequence
<220> FEATURE:
<223> OTHER INFORMATION: Exon 39 forward primer

<400> SEQUENCE: 42
ctgctcattg tcttccccca                                         20

<210> SEQ ID NO 43
<211> LENGTH: 21
<212> TYPE: DNA
<213> ORGANISM: Artificial Sequence
<220> FEATURE:
<223> OTHER INFORMATION: Exon 39 reverse primer

<400> SEQUENCE: 43
caaaccgggc atagacatct g                                       21

<210> SEQ ID NO 44
<211> LENGTH: 5671
<212> TYPE: RNA
<213> ORGANISM: Homo sapiens

<400> SEQUENCE: 44
gugagcauaa cuucuuggc uuuuuguuu gauuaguagg auaguagagu auguguuggu     60
cgagcagagc caggggcaag caucguacau guagcagcug uaugcggaug agugccacuu   120
ucuuccuccc uaccccgac ccugccuccu uuccuuccuu ccuuccuccc auccuuccuu    180
ccucuuuccu ucuuccucc cuccucuccu ccucccccg ucccuccuuc cuuccuuuuu    240
cauugcuucc uuccuuccuu cgucccuccu uccccuuccuc uuuccuucug cccucucucc   300

-continued

| | | |
|---|---|---|
| cuuuuuccuu ucauccuccc uccaucccuc ccuccauccu uccuucuuuc uuccuucuuu | 360 |
| ccuuccuaua agcaccuuuu ucauuucugu gcucugaaug aaaugguuuu cuguguuuau | 420 |
| ucugcaagca aaacuugauu cuugcaauaa acuuaagcu uugcuuacuc uuucagaaag | 480 |
| guuuucucag ggacuuuggg uguuggguuu uacacacaca cacaucaaua cauuugggua | 540 |
| auuucaaaau cuaaaaggaa caaaaaggca uacaaugaaa aaaucuccuu ccuaccccug | 600 |
| uuucccacuc augcaguucu cuucuccaga ggcaaacucu uacuuagagu uccugugugc | 660 |
| ucuggagaca caucagcaga ucccuauacg gucuuucucc cgcuuucuua uggaaauugu | 720 |
| aacacucuga cauauacuau uccuugggca aguuaaucuu gaugaagaga cuggguguuc | 780 |
| uccaugcuga augccucacu uuuaugagcu gccaagccca guugucccuu ccaccugacc | 840 |
| uccccugu cagagacaga uggccaaacu gaaucauaaa aagaggggga aaaaagaag | 900 |
| gcagucgcug cagggcuguc uuuacuccac acuccacacu cccaguccc accgcugugu | 960 |
| cugaguccug gcuguggcug uccuuggaac auuugccuca ccacgugccu guguccccag | 1020 |
| gcgccucaac cuuccucuc cucauuagcu cuuccagu cagagggugg gaccggccag | 1080 |
| cacaucugca cugcugcccu gccacaccca ccuccaccug ccucugggcc cacugggga | 1140 |
| acacaggaca aaucugucg gaggcccac caugaaccgc ccagacccgu ggaccccuga | 1200 |
| gacugacucu uuccagaucu uguuagggu ucguggcugc uaggcaagua acgaagccuc | 1260 |
| aucgucccca ugaaugauaa gaaauucagc augcagagu cagacucugg aaaggcgggg | 1320 |
| ggauaagaac acagcccag cagauggcca gagcacccag gugacugaaa gugcugcuuu | 1380 |
| gcagagcugu guuugccaca ggcucacagc ccacuaaguc uuaagacagu uuccuucag | 1440 |
| aauaauuaaa uagccagcuu aaagcaacuc agaacauuuu ccccucugag gcugcaccca | 1500 |
| uuuagccaac auuugcuaag cacccgccuu caaaaaccug guauuucau guaaauuauc | 1560 |
| cgauacacag cugcuaugga aaccccagu aucccacagg aagcucccca gcucccagca | 1620 |
| gcugccggcc cgugugagau caggaggucu uuaccagcu aacaccacgu gccgggugug | 1680 |
| ugcugauaua aacaagcgug gcccacucgu ccugcccucc agaggcuccc guuccagucg | 1740 |
| gaaaaggacc ugcccacgaa guuugcaacg auauaagcca caguguauga uccuccauaa | 1800 |
| uacagcgugu gacagagcag cagaggagcg aggcagauaa caugcugcag gccagaggca | 1860 |
| gcggaagag ccaggcugca ggggcugggg gagccguggu ggaggaaguu caauuucagc | 1920 |
| cuguagauuu cuauuagccc auuuaauaaa uaaugaagug ccacucuga gcuaaucauu | 1980 |
| gugcagguau uuaggaagga caaaaaaaua auuaggacuc agugcccacc cuccagggc | 2040 |
| ccacugacua guagagaaag uaggcagauu uuuaaaaaau uaaucauggg aaugugauaa | 2100 |
| gugcuggag agaggaaugg auacuuucuc auggaaaucu uggaaggcuu uaagggaag | 2160 |
| gcacucucug agccagcugu cuaaagaaga acaggaaucu uuaagaaagc agaagggaaa | 2220 |
| agagcauucu uuccgcuuug gagcaauagg uaacagccug cacaugccca ggccuagagg | 2280 |
| ccaaagagca cagugauucc agaaagagug gggagaaagg guaggcaggg aaggaugagg | 2340 |
| uaauggggc gcaggugugg aggcuggaga gggaggaggu uguggacug ggaggagcca | 2400 |
| gauggaaugg acagcagugg cccagccagg agcuaugcug gccucguacg ccucgaguguc | 2460 |
| ccuucuauuu ucucagggga ggcucugccc aacaugccaa guccgaccac uugaaaacaa | 2520 |
| guccccuggcu uaacagagac cccagagaga gucuccaacc cuccucuccc uagcaauugg | 2580 |
| uaguugcccu ugaggggcu gaaaagcaga gcuggagaug gcucagggcc ugguguuaac | 2640 |
| aaaugccuug agggcuccug uuguucaaaa gugagucugc agggagagcu cccuaagugg | 2700 |

```
acagcaggag ggcugcagcu ucucugcaca uuccugcugu caccccagag gucaccuagg    2760
ggagggguaa ggacaguaau gcagguuccu cacaguuagc cucggugccc acaugguacu    2820
gagcauagua aauguuuaga agaugcugcc uggcuagaca aaggggaagc ucccgcccac    2880
uagaaacuug cagggagccc caguccuuga uuggucauuu aauugauuag cuccuuggcc    2940
uggccuugag gcacugcuug uaaguacuuc augaccucca uugcaaaccc augaugcucu    3000
gcuggacaaa ucccuccagu ggccagucug gcugcaagga cucucugucu gcaggccuug    3060
cccugugcug uccugugaga gcaucugggc cccaccugcu gaagagaggg ggguggggu     3120 uugccccguu uccaacaguc cuacuucccu guuucagacg cugucaggu caacgccgu      3180 gcugaggaag cugcucauug ucuuccccca cuucugccug gccggggcc ucauugaccu     3240 ugcacugagc caggcuguga cagaugucua ugcccgguuu gguggugu agccgaggcc      3300 cauggagcau gggcccuggg uccaaagcug ggagggguac cgggggggcu ccugcaucag    3360
acuguggcag gggcugggugc uaggaggga ccuuguuggg cuggaggugu ccugccagcu    3420
ggagaggauu aggguugccuc uguuuccaug gcuggggagc cacaggaggg auggagggca   3480
gcccuuauga ggcggugu uggcucugc ucaguuccca cauaaggccu ggucuagugg       3540
gcccugugcu guggccaggu cuguggggug agcuggggcg gcugaagugg acucaauucc    3600
uguugaugcc caggugagga gcacucugca aauccguucc acuggggaccu gauugggaag   3660 aaccuguuug ccauggugu ggaagggug uguacuucc uccugacccu gcugguccag       3720
cgccacuucu uccucuccca augguacguc caugccacac ccugggccag ugggcagcuc    3780
agggcaucca gaacuggacc uuauacccac augguuccauuu cuuccucag gagcccccacu  3840 ccacaauguu uuucuacau ucucaaagcc uggcuuuucu ccaauaauac aaguagagga     3900
ucggguuaaa auaggcacau ucaaauaugu gaagagcauc cacuuuaaaa uauuuaaaau    3960
gcagugcuau uaauuucaau ugcugauuau uaauccuucu cauuuaauua ccaaauguguu   4020 auuuugauua gaugauagua uugcaaauaa caauugguac agggauucca aaguacuagg    4080
aaauagacua auguauuuau gagagaaagg acacagcagg cccccuuugcu aauuagagau   4140 uugggagcau gggaguaaua uggagccau ugggaggggu gcgggcagug aucacgaccc     4200
cccacuccug gaggaaggug gguagcugcc aacccugacu uuugaccagg gcuucucaaa    4260
ugccagguua gcuggcaauu gccauucuuc cgcaggcucu uccugaagcu ggguggcc     4320 cugcccacu ccccucugca auccaguccu accuuuauug uccucacccca ggggccugaa    4380 uugccaagca gcagcccuuc cuagcaagcu uccccaauua guguuuuguu ucuuaacuuu    4440
uccuccucuc aggcugagug uggucaccug uaaauagauu ccaaggacuu gguuuuaugu    4500
uuugauccac agggaauuga uuuauuggaa augaacugc cuuucuacuc acaggacugu    4560
gagaggugaa ugagaucaca ggugucaaca cacgccugau gaaacaggau acacaagcag    4620
uucuaguuau gggagacagu ucaggaauu guugccuug gcacccucag ccccugcaga     4680
cccuuucugc agccuuggcc auaccuuuua gaggcuuuug uggggagag agcaggucag     4740 gagguugacu acccaaauug acucauuagc uucaaacucu gaugucaaca cauuugaaug    4800
aguccugccu gcuuuagggc cuaaagagga ccagagaagu acaccauagu cccggcuuc    4860 cagaagguca gggaggguuu caaagaagag gcugugucuu uaagaauggg gaagauucca   4920 uuugugggg caggaggagg agaacauuga ggacuggaa acacaugcgg aggcuggag      4980 acgggaauga ccaauaggac ugggaaccag ggggagaugc caauugcuga cagaggaguu   5040
```

| | |
|---|---:|
| agugcaagag guaagugaga aggguaggug gggcuggauu gcagggcugu aacuacagcu | 5100 |
| gcagagggag ggcuucaacc uacagcugau ggggaacaac agaagguuuu gaggcaugag | 5160 |
| guggccugau gacaacucug uuuuggaaag guggaguugg cagggcagac uggaggaagu | 5220 |
| ggggaggcucg gagguuagua acuaccccuu acugagugcu ugcuguagag gaagcauuuu | 5280 |
| aguccugacg gugaucccag gcccugaguc uuuacucugu gccaggcacu gugcugaguu | 5340 |
| caucuucagc acaauccuau gagacaggua uguuacccu ccuccucauc acaugguuga | 5400 |
| aguaggcaag guucagagag guccaaugcc caagaucaca caugaggagg ccaggacugg | 5460 |
| aacccaaggc ugacucugga caugagcacc ugaccucucu accuaaugcc uaaugccucu | 5520 |
| ccugcuggga gcccuuuuua gaauuuaagu cuuaaaggau ggaagcccag aaggaagcag | 5580 |
| aagcaaggaa guggaagaga ggucccaugg aaaggacagu gccaaggaca cuguacagcc | 5640 |
| agcccaaucc ugaccccuuu cuucaucua g | 5671 |

<210> SEQ ID NO 45
<211> LENGTH: 3157
<212> TYPE: RNA
<213> ORGANISM: Homo sapiens

<400> SEQUENCE: 45

| | |
|---|---:|
| gugagcauaa cuuucuuggc uuuuuguuu gauuaguagg auaguagagu auguguuggu | 60 |
| cgagcagagc caggggcaag caucguacau guagcagcug uaugcggaug agugccacuu | 120 |
| ucuuccuccc uaccccgac ccugccuccu uccuuccuu ccuccuccc auccuuccuu | 180 |
| ccucuuuccu ucuucccuc cuccucccu ccuuccccg uccuccuuc cuccuuuuu | 240 |
| cauugcuucc uuccuuccuu cgucccuccu ucccuccuc uuccuucug cccucucucc | 300 |
| cuuuuuccuu ucaucucccc uccauccuc cccauccu uccuucuuuc uccuucuuu | 360 |
| ccuuccuaua agcaccuuuu ucauuucugu gcucugaaug aaaugguuuu cuguguuuau | 420 |
| ucugcaagca aaacuugauu cuugcaauaa acuuuaagcu uugcuuacuc uuucagaaag | 480 |
| guuuucucag ggacuuuggg uguggguuu uacacacaca cacaucaaua cauuugggua | 540 |
| auuucaaaau cuaaaaggaa caaaaaggca uacaaugaaa aaaucuccuu ccuaccccug | 600 |
| uuucccacuc augcaguucu cuuccucaga ggcaaacucu acuugaguu ccugugugc | 660 |
| ucuggagaca caucagcaga ucccuauacg gucuuucucc cgcuuucuua uggaaauugu | 720 |
| aacacucuga cauauacuau uccuugggca aguuaaucuu gaugaagaga cugggguguuc | 780 |
| uccaugcuga augccucacu uuuaugagcu gccaagccca guguccuuu ccaccugacc | 840 |
| uccccccuguc cagagacaga uggccaaacu gaaucauaaa aagaggggga aaaaagaag | 900 |
| gcagucgcug cagggcuguc uuuacuccac acuccacacu cccaguccc accgcugugu | 960 |
| cugaguccug gcuguggcug uccuuggaac auuugccuca ccacgugccu gugucccag | 1020 |
| gcgcccucaac cuuccucuc ucauugagcu cuucccaguu cagagggugg gaccggccag | 1080 |
| cacaucugca cugcugcccu gccacacca ccuccaccug ccucugggcc cacuggggga | 1140 |
| acacaggaca aaucugugcg gaggccccac caugaaccgc ccagacccgu gga ccccuga | 1200 |
| gacugacucu uuccagaucu uguuagggu ucgggcugcu aggcaaguaa acgaagccuc | 1260 |
| aucugucccca ugaaugauaa gaaauucagc augucagagu cagacucugg aaaggcgggg | 1320 |
| ggauaagaac acagccccag cagauggcca gagcacccag gugacugaaa gugcugcuuu | 1380 |
| gcagagcugu guuugccaca ggcucacagc ccacuaaguc uuaagacagu uuccuucag | 1440 |
| aauaauuaaa uagccagcuu aaagcaacuc agaacauuuu cccccucugag gcugcaccca | 1500 |

| | | |
|---|---|---|
| uuuagccaac auuugcuaag caccogccuu caaaaaccug guauuuucau guaaauuauc | 1560 |
| cgauacacag cugcuaugga aaccccagu aucccacagg aagcuccca gcucccagca | 1620 |
| gcugccggcc cgugugagau caggaggucu uaccagcug aacaccacgu gccgggugug | 1680 |
| ugcugauaua aacaagcgug gcccacucgu ccugcccucc agaggcuccc guuccagucg | 1740 |
| gaaaaggacc ugcccacgaa guuugcaacg auauaagcca caguguauga uccuccauaa | 1800 |
| uacagcgugu gacagagcag cagaggagcg aggcagauaa caugcugcag gccagaggca | 1860 |
| gcgggaagag ccaggcugca ggggcugggg gagccguggu ggaggaaguu caauuucagc | 1920 |
| cuguagauuu cuauuagccc auuuaauaaa uaaugaagug ccuacucuga gcuaaucauu | 1980 |
| gugcagguau uuaggaagga caaaaaaaua auuaggacuc agugcccacc cuccaggggc | 2040 |
| ccacugacua guagagaaag uaggcagauu uuuaaaaaau uaaucaugggg aaugugauaa | 2100 |
| gugcugggag agaggaaugg auacuuucuc augggaaucu uggaaggcuu guaagggaag | 2160 |
| gcacucucug agccagcugu cuaaagaaga acaggaaucu uuaagaaagc agaagggaaa | 2220 |
| agagcauucu uuccugcuug gagcaauagg uaacagccug cacaugccca ggccuagagg | 2280 |
| ccaaagagca cagugauucc agaaagagug gggagaaagg guaggcaggg aaggaugagg | 2340 |
| uaaugugggc gcaggugugg aggcuggaga gggaggaggu uguggacug ggaggagcca | 2400 |
| gauggaaugg acagcagugg cccagccagg agcuaugcug gccucguacg ccucgauguc | 2460 |
| ccuucuauuu ucucagggga ggcucugccc aacaugccaa guccgaccac uugaaaacaa | 2520 |
| gucccuggcu uaacacagac cccagagaga gucuccaacc cuccucuccc uagacaaugg | 2580 |
| uaguugcccu gugaggggcu gaaaagcaga gcuggagaug gcucagggcc uggguguuaac | 2640 |
| aaaugccuug agggcuccug uuguuucaaa gugagcugc agggagagcu cccuaagugg | 2700 |
| acagcaggag ggcugcagcu ucucugcaca uuccugcugu caccccaga gucaccuagg | 2760 |
| ggaggggluaa ggacaguaau gcagguuccu cacaguuagc cucggugccc acauggguacu | 2820 |
| gagcauagua aauguuuaga agaugcugcc uggcuagaca aaggggaagc ucccgcccac | 2880 |
| uagaaacuug cagggagccc cagccuuga uggucauuu aauugauuag cuccuuggcc | 2940 |
| uggccuugag gcacugcuug uaaguacuuc augaccucca uugcaaaccc augaugcucu | 3000 |
| gcuggacaaa ucccuccagu ggccagucug gcugcaagga cucucugucu gcaggccuug | 3060 |
| cccugugcug uccugugaga gcaucugggc cccaccugcu gaagagaggg ggggugggu | 3120 |
| uugccccguu uccaacaguc cuacuucccu guuucag | 3157 |

<210> SEQ ID NO 46
<211> LENGTH: 124
<212> TYPE: RNA
<213> ORGANISM: Homo sapiens

<400> SEQUENCE: 46

| | | |
|---|---|---|
| acgcugcuca gguucaacgc cgugcugagg aagcugcuca uugucuuccc ccacuucugc | 60 |
| cugggccggg gccucauuga ccuugcacug agccaggcug ugacagaugu cuaugcccgg | 120 |
| uuug | 124 |

<210> SEQ ID NO 47
<211> LENGTH: 332
<212> TYPE: RNA
<213> ORGANISM: Homo sapiens

<400> SEQUENCE: 47

```
guggguggua    gccgaggccc    auggagcaug    ggcccugggu    ccaaagcugg    gagguuacc      60 ggggggcuc     cugcaucaga    cuguggcagg    ggcuggugcu    aggaggggac    cuuguugggc    120 uggaggguguc   cugccagcug    gagaggauua    ggugccucu     guuccaugg     cuggggagcc    180 acaggaggga    uggagggcag    cccuuaugag    gcgggguguuu   ggcucuugcu    caguucccac    240
auaaggccug    gucuagugggg   cccugugcug    uggccagguc    ugugggguga    gcuggggcgg    300
cugaagugga    cucaauuccu    guugaugccc    ag                                        332

<210> SEQ ID NO 48
<211> LENGTH: 130
<212> TYPE: RNA
<213> ORGANISM: Homo sapiens

<400> SEQUENCE: 48
gugaggagca    cucugcaaau    ccguuccacu    gggaccugau    ugggaagaac    cuguuugcca     60
ugguggugga    aggggguggug   uacuuccucc    ugacccugcu    gguccagcgc    cacuucuucc    120
ucucccaaug                                                                          130

<210> SEQ ID NO 49
<211> LENGTH: 1928
<212> TYPE: RNA
<213> ORGANISM: Homo sapiens

<400> SEQUENCE: 49
guacguccau    gccacacccu    gggccagugg    gcagcucagg    gcauccagaa    cuggaccuua     60 ucccacaug     gucauuucuu    uccucaggag    ccccacucca    caauguuuuu    ucuacauucu    120
caaagccugg    cuuuucucca    auaauacaag    uagaggaucg    gguuaaaaua    ggcacauuca    180
aauaugugaa    gagcauccac    uuuaaaauau    uuaaaaugca    gugcuauuaa    uuucaauugc    240
ugauauuuaa    uccuucucau    uuaauuacca    aauguguauu    uugauuagau    gauaguauug    300
caaauaacaa    ugguuacagg    guauccaaag    uacuaggaaa    uagacuaaug    uauuuaugag    360
agaaaggaca    cagcaggccc    cuuugcuaau    uagagauuug    ggagcauggg    aguaauaugg    420
gagccaugug    gagggguguсg   ggcagugauc    acgacccccc    acuccuggag    gaaggugggu    480
agcugccaac    ccugacuuuu    gaccagggcu    ucucaaaugc    cagguuagcu    ggcaauugcc    540
auucuuccgc    aggcucuucc    ugaagcgggu    ugggccccug    ccucacuccc    cucugcaauc    600
caguccuacc    uuuauugucc    ucacccaggg    gccugaauug    ccaagcagca    gcccuuccua    660
gcaagcuuuc    cccauagug    uuuuguuucu     uaacuuuucc    uccucucagg    cugaguguggg   720 ucaccuguaa    auagauucca    aggacuuggu    uuuauguuuu    gauccacagg    gaauugauuu    780
auuggaaaug    aaucugccuu    ucuacucaca    ggacugugag    aggugaauga    gaucacaggu    840
gucaacacac    gccgaugaa    acaggauaca     caagcaguuc    uaguuauggg    agacaguguc    900
aggaauuguu    guccuuggca    cccucagccc    cugcagaccc    uuucugcagc    cuuggccaua    960
ccuuuuagag    gcuuuugugu    gggagagagc    aggucaggag    guugacuacc    caaauugacu   1020
cauuagcuuc    aaacucugau    gucaacacau    uugaaugagu    ccugccugcu    uuagggccua   1080
aagaggacca    gagaaguaca    ccauagcccc    uggcuuccag    aaggucaggg    agggguuucaa  1140 agaagaggcu    gugucuuuaa    gaauggggaa    gauuccauuu    ggugggcag    gaggaggaga    1200 acauugaggg    acuggaaaca    caugcggagg    cugggagacg    ggaaugacca    auaggacugg   1260
gaaccagggg    gagaugccaa    uugcgacag    aggaguuagu     gcaagaggua    agugagaagg   1320
guaggugggg    cuggauugca    gggcuguaac    uacagcugca    gagggagggc    uucaaccuac   1380
```

-continued

```
agcugauggg gaacaacaga agguuuugag gcaugagguG gccugaugac aacucuguuu    1440 uggaagguG gaguuggcag ggcagacuGG aggaaguGGG aggcucggag guuaguaacu    1500
accccuuacu gagugcuugc guagaggaa gcauuuagu ccugacggug aucccaggcc    1560
cugagucuuu acucugugcc aggcacgug cugagucau cuucagcaca auccauagag    1620
acagguauug uuacccuccu ccucaucaca ugguugaagu aggcaagguu cagagagguc    1680
caaugcccaa gaucacacau gaggaggcca ggacuggaac ccaaggcuga cucuggacau    1740
gagcaccuga ccucucuacc uaaugccuaa ugccucuccu gcuggagcc cuuuuuagaa    1800 uuuaagucuu aaaggaugga agcccagaag gaagcagaag caaggaagug aagagaggu    1860 cccauggaaa ggacagugcc aaggacacug uacagccagc ccaauccuga ccccuuuucu    1920
ucaucuag                                                            1928
```

<210> SEQ ID NO 50
<211> LENGTH: 784
<212> TYPE: RNA
<213> ORGANISM: Homo sapiens

<400> SEQUENCE: 50

```
gccuugcccu gugcuguccu gugagagcau cugggcccca ccugcugaag agagggggG    60 uGGGguuugc cccguuucca acaguccuac uucccuguuu cagacgcugc ucagguucaa    120
cgccgugcug aggaagcugc ucauugucuu ccccacuuc ugccugggcc ggggccucau    180
ugaccuugca cugagccagg cuguGacaga ugucuaugcc cgguuuggug ggugguagcc    240
gaggcccaug gagcauGGGc ccuggguccA aagcuGGag ggUUaccggG gGGGCuccuG    300
caucagacug uggcaggGGC uggugcuagg aggggaccuu guuGGGcuGG aggugccug    360 ccagcuggag aggauuaggg ugccucuguu uccauggcug gggagccaca ggagggaugg    420
agggcagccc uuaugaggcg gguguuuggc ucuugcucag uucccacaua aggccuGGuc    480
uagugggccc ugugcugugG ccaggucuGu ggggugagcu gGGGcggcug aaguggacuc    540
aauuccuguu gaugcccagg ugaggagcac ucugcaaauc cguccacug ggaccugauu    600 gggaagaacc uguugccau gguGGugGaa ggggugGUGU acuuccuccu gacccuGcug    660
guccagcgcc acuucuuccu cucccaaugg uacguccaug ccacacccug gccagugGG    720 cagcucaggg cauccagaac uggaccuuau acccacaugG ucauuucuuu ccucaggagc    780
ccca                                                                784
```

<210> SEQ ID NO 51
<211> LENGTH: 33
<212> TYPE: DNA
<213> ORGANISM: Artificial Sequence
<220> FEATURE:
<223> OTHER INFORMATION: MG1-F primer

<400> SEQUENCE: 51

```
aaaaaagtcg acgtgttaac aaatgccttg agg                                33
```

<210> SEQ ID NO 52
<211> LENGTH: 32
<212> TYPE: DNA
<213> ORGANISM: Artificial Sequence
<220> FEATURE:
<223> OTHER INFORMATION: MG1-R primer

<400> SEQUENCE: 52
aaaaaagcgg ccgcagctca ccccacagac ct                                    32

<210> SEQ ID NO 53
<211> LENGTH: 32
<212> TYPE: DNA
<213> ORGANISM: Artificial Sequence
<220> FEATURE:
<223> OTHER INFORMATION: MG3-F primer

<400> SEQUENCE: 53
aaaaaagtcg acaaatccct ccagtggcca gt                                    32

<210> SEQ ID NO 54
<211> LENGTH: 33
<212> TYPE: DNA
<213> ORGANISM: Artificial Sequence
<220> FEATURE:
<223> OTHER INFORMATION: MG3-R primer

<400> SEQUENCE: 54
aaaaaagcgg ccgccctaat cctctccagc tgg                                   33

<210> SEQ ID NO 55
<211> LENGTH: 32
<212> TYPE: DNA
<213> ORGANISM: Artificial Sequence
<220> FEATURE:
<223> OTHER INFORMATION: MG4-R primer

<400> SEQUENCE: 55
aaaaaagcgg ccgcatatca gcaattgaaa tt                                    32

<210> SEQ ID NO 56
<211> LENGTH: 19
<212> TYPE: DNA
<213> ORGANISM: Artificial Sequence
<220> FEATURE:
<223> OTHER INFORMATION: ddPCR forward primer

<400> SEQUENCE: 56
agctctctac ctggtgtgt                                                   19

<210> SEQ ID NO 57
<211> LENGTH: 18
<212> TYPE: DNA
<213> ORGANISM: Artificial Sequence
<220> FEATURE:
<223> OTHER INFORMATION: ddPCR reverse primer

<400> SEQUENCE: 57
aacctgagca gcgtcttg                                                    18

<210> SEQ ID NO 58
<211> LENGTH: 24
<212> TYPE: DNA
<213> ORGANISM: Artificial Sequence
<220> FEATURE:
<223> OTHER INFORMATION: ddPCR probe

<400> SEQUENCE: 58
ttcttctaca cacccatgtc ccgc                                             24

<210> SEQ ID NO 59
<211> LENGTH: 20
<212> TYPE: DNA
<213> ORGANISM: Artificial Sequence
<220> FEATURE:
<223> OTHER INFORMATION: ddPCR forward primer

<400> SEQUENCE: 59
gtcaacagca cctttgtggt                                        20

<210> SEQ ID NO 60
<211> LENGTH: 18
<212> TYPE: DNA
<213> ORGANISM: Artificial Sequence
<220> FEATURE:
<223> OTHER INFORMATION: ddPCR reverse primer

<400> SEQUENCE: 60
tgtgccaccc aaaccggg                                          18

<210> SEQ ID NO 61
<211> LENGTH: 25
<212> TYPE: DNA
<213> ORGANISM: Artificial Sequence
<220> FEATURE:
<223> OTHER INFORMATION: ddPCR probe

<400> SEQUENCE: 61
ggtcaatgag gccccggccc aggca                                  25

<210> SEQ ID NO 62
<211> LENGTH: 20
<212> TYPE: DNA
<213> ORGANISM: Artificial Sequence
<220> FEATURE:
<223> OTHER INFORMATION: ddPCR forward primer

<400> SEQUENCE: 62
gtcaacagca cctttgtggt                                        20

<210> SEQ ID NO 63
<211> LENGTH: 20
<212> TYPE: DNA
<213> ORGANISM: Artificial Sequence
<220> FEATURE:
<223> OTHER INFORMATION: ddPCR reverse primer

<400> SEQUENCE: 63
caaggtctga aggtcacggg                                        20

<210> SEQ ID NO 64
<211> LENGTH: 21
<212> TYPE: DNA
<213> ORGANISM: Artificial Sequence
<220> FEATURE:
<223> OTHER INFORMATION: ddPCR probe

<400> SEQUENCE: 64
aggacccaca aggtggcaca a                                      21

<210> SEQ ID NO 65
<211> LENGTH: 34
<212> TYPE: RNA
<213> ORGANISM: Homo sapiens

<400> SEQUENCE: 65
ugguagccga ggcccaugga gcaugggccc uggg                        34

<210> SEQ ID NO 66

<211> LENGTH: 31
<212> TYPE: RNA
<213> ORGANISM: Homo sapiens

<400> SEQUENCE: 66
uugcccugug cguccugug agagcaucug g                    31

<210> SEQ ID NO 67
<211> LENGTH: 1808
<212> TYPE: DNA
<213> ORGANISM: Artificial Sequence
<220> FEATURE:
<223> OTHER INFORMATION: MG3_2 mini gene insert

<400> SEQUENCE: 67

| | | | | | |
|---|---|---|---|---|---|
| gaattccgga | ggtcaacaac | gagtcttttg | tcatctacat | gttcgtggtc | cacttcacca | 60 |
| tccccatgat | tatcatcttt | ttctgctatg | ggcagctcgt | cttcaccgtc | aaggaggtac | 120 |
| gggccggggg | gtgggcggcc | tcacggctct | gagggtccag | ccccagcat | gcatctgcgg | 180 |
| ctcctgctcc | ctggaggagc | catatcacaa | gtttgtacaa | aaaagcaggc | ttcgtgttaa | 240 |
| caaatgcctt | gagggctcct | gttgtttcaa | agtgagtctg | cagggagagc | tccctaagtg | 300 |
| gacagcagga | gggctgcagc | ttctctgcac | attcctgctg | tcaccccag | agtcacctag | 360 |
| ggaggggta | aggacagtaa | tgcaggttcc | tcacagttag | cctcggtgcc | cacatggtac | 420 |
| tgagcatagt | aaatgtttag | aagatgctgc | ctggctagac | aaaggggaag | ctcccgccca | 480 |
| ctagaaactt | gcagggagcc | ccagtccttg | attggtcatt | taattgatta | gctccttggc | 540 |
| ctggccttga | ggcactgctt | gtaagtactt | catgacctcc | attgcaaacc | catgatgctc | 600 |
| tgctggacaa | atccctccag | tggccagtct | ggctgcaagg | actctctgtc | tgcaggcctt | 660 |
| gccctgtgct | gtcctgtgag | agcatctggg | ccccacctgc | tgaagagagg | ggggtgggg | 720 |
| tttgccccgt | ttccaacagt | cctacttccc | tgtttcagac | gctgctcagg | ttcaacgccg | 780 |
| tgctgaggaa | gctgctcatt | gtcttccccc | acttctgcct | gggccgggc | ctcattgacc | 840 |
| ttgcactgag | ccaggctgtg | acagatgtct | atgcccggtt | tggtgggtgg | tagccgaggc | 900 |
| ccatggagca | tgggccctgg | gtccaaagct | gggagggtta | ccggggggc | tcctgcatca | 960 |
| gactgtggca | ggggctggtg | ctaggagggg | accttgttgg | gctggaggtg | tcctgccagc | 1020 |
| tggagaggat | tagggtgcct | ctgtttccat | ggctggggag | ccacaggagg | gatggagggc | 1080 |
| agcccttatg | aggcgggtgt | ttggctcttg | ctcagttccc | acataaggcc | tggtctagtg | 1140 |
| ggccctgtgc | tgtggccagg | tctgtggggt | gagctgaccc | agctttcttg | tacaaagtgg | 1200 |
| tgatgagagg | tacctccgag | gggtaaacag | ttgggtaaac | agtctctgaa | gtcagctctg | 1260 |
| ccattttcta | gctgtatggc | cctgggcaag | tcaatttcct | tctctgtgct | ttggtttcct | 1320 |
| catccataga | aaggtagaaa | gggcaaaaca | ccaaactctt | ggattacaag | agataattta | 1380 |
| cagaacaccc | ttggcacaca | gagggcacca | tgaaatgtca | cgggtgacac | agccccttg | 1440 |
| tgctcagtcc | ctggcatctc | tagggggtgag | gagcgtctgc | ctagcaggtt | cccaccagga | 1500 |
| agctggattt | gagtggatgg | ggcgctggaa | tcgtgagggg | cagaagcagg | caaagggtcg | 1560 |
| gggcgaacct | cactaacgtg | ccagttccaa | gcacactgtg | ggcagccctg | gccctgactc | 1620 |
| aagcctcttg | ccttccagtt | ccggaactgc | atgctcacca | ccatctgctg | cggcaagaac | 1680 |
| ccactgggtg | acgatgaggc | ctctgctacc | gtgtccaaga | cggagacgag | ccaggtggcc | 1740 |
| ccggcctaag | acctgcctag | gactctgtgg | ccgactatag | gcgtctccca | tccctacac | 1800 |
| ctgtcgac | | | | | | 1808 |

<210> SEQ ID NO 68
<211> LENGTH: 110
<212> TYPE: DNA
<213> ORGANISM: Homo sapiens

<400> SEQUENCE: 68
cggaggtcaa caacgagtct tttgtcatct acatgttcgt ggtccacttc accatcccca      60
tgattatcat cttttctgc tatgggcagc tcgtcttcac cgtcaaggag                 110

<210> SEQ ID NO 69
<211> LENGTH: 111
<212> TYPE: DNA
<213> ORGANISM: Homo sapiens

<400> SEQUENCE: 69
ttccggaact gcatgctcac caccatctgc tgcggcaaga acccactggg tgacgatgag      60
gcctctgcta ccgtgtccaa gacggagacg agccaggtgg ccccggccta a              111

<210> SEQ ID NO 70
<211> LENGTH: 21
<212> TYPE: DNA
<213> ORGANISM: Artificial Sequence
<220> FEATURE:
<223> OTHER INFORMATION: ddPCR forward primer

<400> SEQUENCE: 70
tacatgttcg tggtccactt c                                                21

<210> SEQ ID NO 71
<211> LENGTH: 21
<212> TYPE: DNA
<213> ORGANISM: Artificial Sequence
<220> FEATURE:
<223> OTHER INFORMATION: ddPCR reverse primer

<400> SEQUENCE: 71
gaagacaatg agcagcttcc t                                                21

<210> SEQ ID NO 72
<211> LENGTH: 21
<212> TYPE: DNA
<213> ORGANISM: Artificial Sequence
<220> FEATURE:
<223> OTHER INFORMATION: ddPCR probe

<400> SEQUENCE: 72
aacgctgctc aggttcaacg c                                                21

<210> SEQ ID NO 73
<211> LENGTH: 18
<212> TYPE: DNA
<213> ORGANISM: Artificial Sequence
<220> FEATURE:
<223> OTHER INFORMATION: ddPCR reverse primer

<400> SEQUENCE: 73
gcagatggtg gtgagcat                                                    18

<210> SEQ ID NO 74

```
<211> LENGTH: 23
<212> TYPE: DNA
<213> ORGANISM: Artificial Sequence
<220> FEATURE:
<223> OTHER INFORMATION: ddPCR probe

<400> SEQUENCE: 74
accgtcaagg agttccggaa ctg                                              23
```